US009622888B2

(12) United States Patent
Armstrong et al.

(10) Patent No.: US 9,622,888 B2
(45) Date of Patent: Apr. 18, 2017

(54) STENT HAVING FLEXIBLY CONNECTED ADJACENT STENT ELEMENTS

(75) Inventors: Joseph R. Armstrong, Flagstaff, AZ (US); Edward H. Cully, Flagstaff, AZ (US); Mark Y. Hansen, Flagstaff, AZ (US); Brian L. Johnson, Flagstaff, AZ (US); Bret J. Kilgrow, Flagstaff, AZ (US); Larry J. Kovach, Flagstaff, AZ (US); James D. Silverman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 578 days.

(21) Appl. No.: 11/560,774

(22) Filed: Nov. 16, 2006

(65) Prior Publication Data

US 2008/0119943 A1 May 22, 2008

(51) Int. Cl.
*A61F 2/06* (2013.01)
*A61F 2/89* (2013.01)
*A61F 2/07* (2013.01)
*A61F 2/82* (2013.01)

(52) U.S. Cl.
CPC .......... *A61F 2/89* (2013.01); *A61F 2002/075* (2013.01); *A61F 2002/825* (2013.01); *A61F 2002/828* (2013.01)

(58) Field of Classification Search
CPC ......... A61F 2/07; A61F 2/88; A61F 2002/075
USPC ................................................ 623/1.14, 1.13
See application file for complete search history.

(56) References Cited

U.S. PATENT DOCUMENTS

| 4,503,569 | A | 3/1985 | Dotter |
| 4,655,771 | A | 4/1987 | Wallsten |
| 4,739,762 | A | 4/1988 | Palmaz |
| 4,776,337 | A | 10/1988 | Palmaz |
| 5,019,090 | A | 5/1991 | Pinchuk |
| 5,037,427 | A | 8/1991 | Harada et al. |
| 5,061,275 | A | 10/1991 | Wallsten et al. |
| 5,102,417 | A | 4/1992 | Palmaz |
| 5,104,404 | A | 4/1992 | Wolff |

(Continued)

FOREIGN PATENT DOCUMENTS

| EP | 0 951 877 | 10/1999 |
| EP | 1110561 | 6/2001 |

(Continued)

OTHER PUBLICATIONS

Wilson EP, White RA, Kopchok GE, et al. Deployment and Healing of an ePTFE Encapsulated Stent Endograft in the Canine Aorta. Annals of Vascular Surgery 1997; v11, No. 4:354-358.

(Continued)

*Primary Examiner* — Brian Dukert

(57) ABSTRACT

An open stent (a stent having open space through its thickness at locations between the ends of the stent), incorporating flexible, preferably polymeric, connecting elements into the stent wherein these elements connect adjacent, spaced-apart stent elements. Preferably the spaced-apart adjacent stent elements are the result of forming the stent from a helically wound serpentine wire having space provided between adjacent windings. Other stent forms such as multiple, individual spaced-apart ring-shaped or interconnected stent elements may also be used. The connecting elements are preferably longitudinally oriented.

15 Claims, 15 Drawing Sheets

(56) References Cited

U.S. PATENT DOCUMENTS

| | | |
|---|---|---|
| 5,122,154 A | 6/1992 | Rhodes |
| 5,123,917 A | 6/1992 | Lee |
| 5,201,757 A | 4/1993 | Heyn et al. |
| 5,236,447 A | 8/1993 | Kubo et al. |
| 5,282,824 A | 2/1994 | Gianturco |
| 5,300,500 A | 4/1994 | Lee et al. |
| 5,314,472 A | 5/1994 | Fontaine |
| 5,330,500 A | 7/1994 | Song |
| 5,360,443 A | 11/1994 | Barone et al. |
| 5,405,377 A | 4/1995 | Cragg |
| 5,443,496 A | 8/1995 | Schwartz et al. |
| 5,443,499 A | 8/1995 | Schmitt |
| 5,449,373 A | 9/1995 | Pinchasik et al. |
| 5,507,767 A | 4/1996 | Maeda et al. |
| 5,507,771 A | 4/1996 | Gianturco |
| 5,549,663 A | 8/1996 | Cottone, Jr. |
| 5,575,816 A | 11/1996 | Rudnick et al. |
| 5,591,195 A | 1/1997 | Taheri et al. |
| 5,662,703 A | 9/1997 | Yurek et al. |
| 5,665,115 A | 9/1997 | Cragg |
| 5,674,241 A | 10/1997 | Bley et al. |
| 5,683,448 A | 11/1997 | Cragg |
| 5,693,086 A | 12/1997 | Goicoechea et al. |
| 5,725,570 A | 3/1998 | Heath |
| 5,728,150 A | 3/1998 | McDonald et al. |
| 5,735,892 A | 4/1998 | Myers et al. |
| 5,755,774 A | 5/1998 | Pinchuk |
| 5,756,553 A | 5/1998 | Iguchi et al. |
| 5,769,884 A * | 6/1998 | Solovay .................. 623/1.13 |
| 5,769,887 A | 6/1998 | Brown et al. |
| 5,800,456 A | 9/1998 | Maeda et al. |
| 5,800,515 A | 9/1998 | Nadal et al. |
| 5,800,521 A | 9/1998 | Orth |
| 5,814,063 A | 9/1998 | Freitag |
| 5,824,043 A | 10/1998 | Cottone, Jr. |
| 5,824,059 A | 10/1998 | Wijay |
| 5,843,161 A | 12/1998 | Solovay |
| 5,873,906 A | 2/1999 | Lau et al. |
| 5,876,432 A | 3/1999 | Lau et al. |
| 5,891,193 A | 4/1999 | Robinson et al. |
| 5,899,934 A | 5/1999 | Amundson et al. |
| 5,906,639 A | 5/1999 | Rudnick et al. |
| 5,919,225 A | 7/1999 | Lau et al. |
| 5,922,020 A | 7/1999 | Klein et al. |
| 5,968,091 A | 10/1999 | Pinchuk et al. |
| 5,984,957 A | 11/1999 | Laptewicz, Jr. et al. |
| 6,001,125 A | 12/1999 | Golds et al. |
| 6,004,348 A | 12/1999 | Banas et al. |
| 6,013,854 A * | 1/2000 | Moriuchi .................. 623/1.11 |
| 6,015,432 A | 1/2000 | Rakos et al. |
| 6,016,846 A | 1/2000 | Knittel et al. |
| 6,022,374 A | 2/2000 | Imran |
| 6,048,360 A | 4/2000 | Khosravi et al. |
| 6,071,307 A * | 6/2000 | Rhee .................. A61F 2/07 623/1.13 |
| 6,077,296 A | 6/2000 | Shokoohi et al. |
| 6,107,004 A | 8/2000 | Donadio, III |
| 6,139,573 A | 10/2000 | Sogard et al. |
| 6,139,575 A | 10/2000 | Shu et al. |
| 6,143,022 A | 11/2000 | Shull et al. |
| 6,146,417 A | 11/2000 | Ischinger |
| 6,159,239 A | 12/2000 | Greenhalgh |
| 6,165,210 A | 12/2000 | Lau et al. |
| 6,171,334 B1 | 1/2001 | Cox |
| 6,174,328 B1 | 1/2001 | Cragg |
| 6,217,609 B1 | 4/2001 | Haverkost |
| 6,231,597 B1 | 5/2001 | Deem et al. |
| 6,264,687 B1 | 7/2001 | Tomonto |
| 6,283,992 B1 | 9/2001 | Hankh et al. |
| 6,287,333 B1 | 9/2001 | Appling et al. |
| 6,290,722 B1 | 9/2001 | Wang |
| 6,312,458 B1 | 11/2001 | Golds |
| 6,315,791 B1 | 11/2001 | Gingras et al. |
| 6,315,792 B1 | 11/2001 | Armstrong et al. |
| 6,331,188 B1 | 12/2001 | Lau et al. |
| 6,331,190 B1 | 12/2001 | Shokoohi et al. |
| 6,334,868 B1 | 1/2002 | Ham |
| 6,336,937 B1 | 1/2002 | Vonesh et al. |
| 6,340,366 B2 | 1/2002 | Wijay |
| 6,344,054 B1 | 2/2002 | Parodi |
| 6,350,277 B1 | 2/2002 | Kocur |
| 6,355,055 B1 | 3/2002 | Waksman et al. |
| 6,357,104 B1 | 3/2002 | Myers |
| 6,361,637 B2 | 3/2002 | Martin et al. |
| 6,364,903 B2 | 4/2002 | Tseng et al. |
| 6,387,122 B1 | 5/2002 | Cragg |
| 6,398,803 B1 * | 6/2002 | Layne .................. A61F 2/07 623/1.13 |
| 6,409,754 B1 | 6/2002 | Smith et al. |
| 6,432,133 B1 | 8/2002 | Lau et al. |
| 6,436,132 B1 * | 8/2002 | Patel et al. .................. 623/1.13 |
| 6,451,050 B1 | 9/2002 | Rudakov et al. |
| 6,461,380 B1 | 10/2002 | Cox |
| 6,488,701 B1 | 12/2002 | Nolting et al. |
| 6,488,705 B2 | 12/2002 | Schmitt et al. |
| 6,497,722 B1 | 12/2002 | Von Oepen et al. |
| 6,500,203 B1 | 12/2002 | Thompson et al. |
| 6,503,556 B2 | 1/2003 | Harish et al. |
| 6,511,496 B1 | 1/2003 | Huter et al. |
| 6,520,986 B2 | 2/2003 | Martin et al. |
| 6,537,311 B1 | 3/2003 | Cox et al. |
| 6,540,773 B2 | 4/2003 | Dong |
| 6,540,776 B2 | 4/2003 | Sanders Millare et al. |
| 6,551,350 B1 | 4/2003 | Thornton et al. |
| 6,551,352 B2 | 4/2003 | Clerc et al. |
| 6,558,414 B2 | 5/2003 | Layne |
| 6,558,415 B2 | 5/2003 | Thompson |
| 6,565,599 B1 | 5/2003 | Hong et al. |
| 6,585,755 B2 | 7/2003 | Jackson et al. |
| 6,589,275 B1 | 7/2003 | Ivancev et al. |
| 6,589,276 B2 | 7/2003 | Pinchasik et al. |
| 6,602,284 B2 | 8/2003 | Cox et al. |
| 6,607,551 B1 | 8/2003 | Sullivan et al. |
| 6,616,689 B1 | 9/2003 | Ainsworth et al. |
| 6,626,939 B1 | 9/2003 | Burnside et al. |
| 6,629,992 B2 | 10/2003 | Bigus et al. |
| 6,645,239 B1 | 11/2003 | Park et al. |
| 6,652,574 B1 | 11/2003 | Jayaraman |
| 6,652,579 B1 | 11/2003 | Cox et al. |
| 6,669,719 B2 | 12/2003 | Wallace et al. |
| 6,673,103 B1 | 1/2004 | Golds et al. |
| 6,689,162 B1 | 2/2004 | Thompson |
| 6,709,454 B1 | 3/2004 | Cox et al. |
| 6,713,357 B1 | 3/2004 | Wang et al. |
| 6,730,117 B1 | 5/2004 | Tseng et al. |
| 6,740,114 B2 | 5/2004 | Burgermeister |
| 6,770,087 B2 | 8/2004 | Layne et al. |
| 6,770,089 B1 | 8/2004 | Hong et al. |
| 6,805,705 B2 | 10/2004 | Hong et al. |
| 6,849,086 B2 | 2/2005 | Cragg |
| 6,866,805 B2 | 3/2005 | Hong et al. |
| 6,872,433 B2 | 3/2005 | Seward et al. |
| 6,881,221 B2 | 4/2005 | Golds |
| 6,887,266 B2 | 5/2005 | Williams et al. |
| 6,893,457 B2 | 5/2005 | Dong |
| 6,945,991 B1 | 9/2005 | Brodeur et al. |
| 7,105,018 B1 | 9/2006 | Yip et al. |
| 7,105,021 B2 | 9/2006 | Edens et al. |
| 7,108,716 B2 | 9/2006 | Burnside et al. |
| 7,112,293 B2 | 9/2006 | Dubson et al. |
| 7,115,220 B2 | 10/2006 | Dubson et al. |
| 7,118,592 B1 | 10/2006 | Dang et al. |
| 7,141,062 B1 | 11/2006 | Pinchasik et al. |
| 7,144,422 B1 | 12/2006 | Rao |
| 7,163,553 B2 | 1/2007 | Limon |
| 7,186,263 B2 | 3/2007 | Golds et al. |
| 7,273,495 B2 | 9/2007 | Limon |
| 7,288,111 B1 | 10/2007 | Holloway et al. |
| 7,323,008 B2 | 1/2008 | Kantor et al. |
| 7,329,276 B2 | 2/2008 | Smith et al. |
| 7,455,687 B2 | 11/2008 | Saunders et al. |
| 7,691,461 B1 | 4/2010 | Prabhu |
| 7,704,274 B2 * | 4/2010 | Boyle et al. .................. 623/1.13 |
| 7,727,271 B2 | 6/2010 | Kujawski et al. |

(56) References Cited

U.S. PATENT DOCUMENTS

| | | |
|---|---|---|
| 8,926,688 B2 | 1/2015 | Burkart et al. |
| 2001/0020181 A1 | 9/2001 | Layne |
| 2001/0025130 A1 | 9/2001 | Tomonto |
| 2002/0007102 A1 | 1/2002 | Salmon et al. |
| 2002/0111668 A1 | 8/2002 | Smith |
| 2002/0151964 A1 | 10/2002 | Smith et al. |
| 2002/0165601 A1 | 11/2002 | Clerc |
| 2003/0208260 A1 | 11/2003 | Lau et al. |
| 2004/0019373 A1 | 1/2004 | Casey, II et al. |
| 2004/0024442 A1 | 2/2004 | Sowinski et al. |
| 2004/0024448 A1 | 2/2004 | Chang et al. |
| 2004/0030377 A1 | 2/2004 | Dubson et al. |
| 2004/0096532 A1 | 5/2004 | Dubson et al. |
| 2004/0096533 A1 | 5/2004 | Dubson et al. |
| 2004/0167635 A1 | 8/2004 | Yachia et al. |
| 2004/0172127 A1 | 9/2004 | Kantor |
| 2004/0236402 A1 | 11/2004 | Layne et al. |
| 2005/0010281 A1 | 1/2005 | Yodfat et al. |
| 2005/0125071 A1 | 6/2005 | Nahleili |
| 2005/0137675 A1 | 6/2005 | Dubson et al. |
| 2005/0154449 A1 | 7/2005 | Elmaleh |
| 2005/0182474 A1 | 8/2005 | Jones et al. |
| 2005/0186243 A1 | 8/2005 | Hunter et al. |
| 2005/0228480 A1 | 10/2005 | Douglas et al. |
| 2006/0009835 A1 | 1/2006 | Osborne et al. |
| 2006/0036308 A1 | 2/2006 | Goshgarian |
| 2006/0036311 A1 | 2/2006 | Nakayama et al. |
| 2006/0085065 A1 | 4/2006 | Krause et al. |
| 2006/0122691 A1 | 6/2006 | Richter |
| 2006/0184237 A1 | 8/2006 | Weber et al. |
| 2006/0259133 A1 | 11/2006 | Sowinski et al. |
| 2006/0266474 A1 | 11/2006 | Burnside et al. |
| 2006/0271157 A1 | 11/2006 | Edens et al. |
| 2006/0271165 A1 | 11/2006 | Yip et al. |
| 2006/0287709 A1 | 12/2006 | Rao |
| 2006/0293743 A1 | 12/2006 | Andersen et al. |
| 2007/0055365 A1 | 3/2007 | Greenberg et al. |
| 2007/0073383 A1 | 3/2007 | Yip et al. |
| 2007/0129791 A1 | 6/2007 | Balaji |
| 2007/0208412 A1 | 9/2007 | Elmaleh |
| 2007/0250146 A1 | 10/2007 | Cully et al. |

FOREIGN PATENT DOCUMENTS

| | | |
|---|---|---|
| EP | 1927327 | 6/2008 |
| WO | 95/26695 | 4/1995 |
| WO | 96/21404 | 7/1996 |
| WO | 99/34855 | 7/1999 |
| WO | 00/42949 | 7/2000 |
| WO | 00/49971 | 8/2000 |
| WO | 01/21101 | 3/2001 |
| WO | 03/057075 | 7/2003 |
| WO | 03/057077 | 7/2003 |
| WO | 2005/096997 | 10/2005 |
| WO | 2006/029617 | 3/2006 |
| WO | 2006/124824 | 11/2006 |

OTHER PUBLICATIONS

Nakayama Y, Nishi S, Ueda H, et al. Fabrication of micropored elastomeric film covered stents and acute-phase performances. Development of Covered Stents 2002; 52-61.

Nishi S, Nakayama Y, Ueda H, et al. Newly developed stent graft with micropored and heparin impregnated SPU film Long-term follow-up study in vivo. 2001 (Suppl 1) 161-166.

* cited by examiner

STENT HAVING FLEXIBLY CONNECTED ADJACENT STENT ELEMENTS

FIELD OF THE INVENTION

The present invention relates to the field of implantable stents having flexibly connected adjacent stent elements.

BACKGROUND OF THE INVENTION

The use of implantable stents in the vasculature and other body conduits has become commonplace since first proposed by Dotter in the 1960's. These devices were required to have a small, compacted diameter for insertion into the intended body conduit and transport, typically via a catheter, to a desired site for deployment, at which site they were expanded to a larger diameter as necessary to fit interferably with the luminal surface of the body conduit. They developed into balloon expandable stents that were expanded by plastically deforming the device with an inflatable balloon on which the expandable stent was mounted in the compacted state, the balloon being attached to the distal end of the catheter and inflated via the catheter. Self-expanding stents subsequently evolved, these devices being forcibly compacted to a small diameter and restrained at that diameter by a sleeve or other means. Following delivery to a desired site for deployment, they are released from the restraint and spring open to meet the luminal surface of the body conduit. These devices are typically made from nitinol metal alloys and typically rely on the superelastic and biocompatible character of this metal. Nitinol stents that rely on the shape memory attributes of that material are also known.

The evolution of implantable stents included the use of a tubular covering fitted to the stent, either to the outer or the luminal surface (or both surfaces) of the stent. These covered stents have generally come to be referred to as stent-grafts. The coverings were generally of a polymeric biocompatible material such as polyethylene terephthalate (PET) or polytetrafluoroethylene (PTFE). See, for example, U.S. Pat. No. 4,776,337 to Palmaz. This patent also describes that the covering may be optionally provided with perforations if desired for particular applications. Because of the open area provided by the perforations, such devices having perforated coverings may be considered to be a sort of hybrid stent and stent-graft, as are devices that include stent frame having metallic stent elements and polymeric elements connecting, covering or other otherwise being attached to the stent elements. The presence of the polymeric elements reduces the otherwise open space between the adjacent metallic stent elements, either very slightly or very substantially depending on the intended application and mechanical design.

Generally, a fully covered stent-graft can be considered to have a surface area (hereinafter $A_{max}$) equal to the circumference of the expanded stent multiplied by the length of the stent. For a conventional, open frame stent (as opposed to a stent-graft), the surface area represented by all of the stent elements is only a small portion of the maximum surface area $A_{max}$. The actual surface area covered by the stent, meaning the area covered by all components of the stent (including connecting elements) in their deployed state, is $A_{stent}$. The porosity index, or P.I., describes the open area (the portion of the maximum surface area not covered by all components of the stent assembly) as a percentage of maximum surface area, wherein:

$$P.I.=(1-(A_{stent}/A_{max}))\times 100\%.$$

The open area may be a continuous single space, such as the space between windings of a single helically wound stent element. Likewise the open area may be represented by the space between multiple individual annular or ring-shaped stent elements. The open area may also be represented by the total area of multiple apertures provided by either a single stent element (e.g., as shown by FIGS. 1B and 2B of U.S. Pat. No. 4,776,337) or by multiple stent elements providing multiple apertures. If multiple apertures are provided they may be of equal or unequal sizes. The use of a perforated graft covering or of polymeric elements in addition to metallic stent elements may also reduce the open area.

Stents having a porosity index of greater than 50% are considered to be substantially open stents.

In addition to the porosity index, the size of any aperture providing the open area must be considered if it is intended to cover only a portion of a stent area for a specific stent application. For multiple apertures, often the consideration must be for the largest size of any individual aperture, particularly if the apertures are to provide for a "filtering" effect whereby they control or limit the passage of biologic materials from the luminal wall into the flow space of the body conduit.

Various stent devices combining metallic stent elements with polymeric connecting elements are known; see, for example U.S. Pat. No. 5,507,767 to Maeda et al. Another is a stent provided with a flexible knitted sleeve having small open apertures in the fashion of chain link fencing, from InspireMD Ltd. (4 Derech Hashalom St., Tel Aviv 67892 Israel). Perforated stent-grafts are also known; see, for example WO00/42949.

SUMMARY OF THE INVENTION

The present invention relates to several approaches to creating an open stent, that is, a stent having open space through its thickness at locations between the ends of the stent, by incorporating flexible, preferably polymeric connecting elements into the stent wherein these elements connect adjacent, spaced-apart stent elements. Preferably the spaced-apart adjacent stent elements are the result of forming the stent from a helically wound serpentine wire having space provided between adjacent windings. Other stent forms such as multiple, individual spaced-apart ring-shaped stent elements may also be used as will be described, but embodiments presented that utilize the helically wound serpentine forms are preferred for many applications.

The adjacent, spaced-apart stent elements are substantially circumferentially oriented, meaning that they have a general direction of orientation perpendicular to the longitudinal axis of the stent, when the stent is in a straight (unbent state) form, plus or minus 45°.

The flexible, preferably polymeric connecting elements provide a means for keeping the stent elements equally spaced and allow the construction of a stent having good flexibility. These flexible connecting elements are preferably substantially oriented in a longitudinal direction with respect to the stent, meaning that they are more longitudinally oriented than circumferentially oriented. They may range in orientation from being perfectly parallel to the longitudinal axis of the stent (when the stent is in a straight, unbent form) up to an angle of 45° from the longitudinal axis. More particularly, they may be oriented at angles of less than or equal to about 45°, 40°, 35°, 30°, 25°, 20°, 15°, 10°, 5°, 4°, 3°, 2° or 1° from the longitudinal axis, or may be virtually parallel to the longitudinal axis of the stent. Being parallel to the longitudinal axis or close to parallel (e.g., +/−50) is preferred.

The described stents have very good porosity index values, typically at least 50% and may be made to be at least 55%, 60%, 65%, 70%, 75%, 80%, 85%, 90%, 95% or 97%. These stents can be considered to be substantially open.

The flexible connecting elements may optionally provide a substrate for the delivery of therapeutic agents such as drugs, which may be intended for any of a variety of medical purposes. Coatings for other purposes (e.g., to render the surface hydrophilic) may also be applied.

The stent may also be designed to allow it to be removed after its primary therapeutic effect has occurred. The stent may be removed by including elements that may be snared with an intravascular snare.

While polymeric materials are preferred as the connecting elements, other non-polymeric materials such as nitinol wire offer good flexibility and may also be used.

A helically wound, undulating or serpentine metal wire stent structure provides good flexibility and is preferred for providing the necessary stent structure having spaced apart stent elements. These structures and other stent structures may be used for self-expanding or balloon expandable stents made respectively from (for example) nitinol or stainless steel. While metal wire is preferred for structures of this type, they may also be made from metal tubing by various known machining methods.

While metal materials are preferred, the stent elements may optionally be made of various polymeric materials that offer suitable physical and mechanical properties and may offer other unique properties desired for specific applications (such as, for example, bioabsorbable polymers).

The first fundamental embodiment is a stent structure wherein at least one substantially longitudinally oriented flexible, preferably polymeric strip is used to maintain spacing of adjacent stent elements, such as the adjacent windings of a helical stent form. More than one such strip may be used, with multiple strips (two or more) preferably being spaced apart equal circumferential distances around the circumference of the stent. While the orientation of the strip or strips is primarily longitudinal, it may also have a helical component such that it is not parallel to the longitudinal axis of the stent when the stent is in a straight or 'unbent' state. The strip is substantially longitudinally oriented if it is parallel to the longitudinal axis of the stent when it is in the straight or unbent state, plus or minus 45°. The use of the substantially longitudinally oriented strip results in a flexible stent with good bending properties. The strip limits elongation of the stent, particularly during expansion of the stent from a compacted diameter to a fully deployed diameter. It also limits foreshortening of the stent, also particularly during expansion.

A second fundamental embodiment, which may also be based on the helically wound serpentine wire form, uses a flexible, preferably polymeric filament laced along the length of the stent to locate the adjacent stent elements (e.g., adjacent helical windings) with respect to each other. This filament is preferably laced so that it includes a transversely oriented loop around one half of a full sinusoid of the serpentine wire, with these loops created around sequential sinusoids along the length of the stent that are preferably axially aligned. One or more of these filament lacings may be provided along the length of the stent. When more than one lacing filament is used, they are preferably spaced apart in equal circumferential amounts (e.g., if three lacing filaments are used along the length of the stent, they are preferably spaced 120° apart).

A third fundamental embodiment includes a stent provided with a perforated covering of a flexible, preferably polymeric graft material, in the form of a sheet of material rolled and preferably seamed to form a tube, or alternatively as a seamless integral tube, that is provided with a multiplicity of perforations or apertures. The covering material is thus integral or monolithic as opposed to being created from separate filaments, threads or other assembled components with multiple crossover points that add to thickness and may be vulnerable to breakage and consequent unraveling of the covering. The perforated covers described are used to connect adjacent spaced apart stent elements and may also be used with a variety of stent forms including separate rings, helically wound wires, machined metal tubes, etc. The perforated covering is thin, strong and flexible and, in combination with the stent elements, results in a flexible, thin and strong stent. Perforation sizes may be as desired, with relatively small perforations on the order of 0.10 mm (minimum aperture size) being preferred for carotid applications where it is desirable to minimize risk of introduction of emboli into a bloodstream. Larger apertures (for example 1, 2 or even 5 mm) may be preferred for larger diameter vessels (e.g., the thoracic arch) where it may be desired to stent the arch (for example, in the treatment of a dissection and/or containment of emboli) while allowing blood flow to side branches through the apertures of the graft material. These embodiments preferably have high porosity indices and preferably incorporate hexagonal apertures, although other shapes are possible.

It is also possible to combine the different stent element connecting techniques described herein.

DETAILED DESCRIPTION OF THE DRAWINGS

Several open frame stent designs are presented, wherein adjacent stent elements are connected by flexible connecting elements. These flexible connecting elements are typically polymeric and may take various forms such as strips, filaments or perforated sheets. Typical stent forms are helically wound metallic wire (e.g., nitinol or stainless steel) or multiple ring-shaped metallic stent elements. The helically wound wire is preferably serpentine wire as will be further described. The serpentine wire may also be oriented circumferentially in the fashion of individual rings or may alternatively be a single continuous wire arranged as will be described. In addition to wire forms, various other stent forms, typically metallic but not limited to metallic, may also be created that lend themselves to the present invention. Among these are machined tubular forms wherein individual ring-shapes, or alternatively perforated tubes or other forms (e.g., helical) that extend continuously between opposing ends of the stent.

Figure 1:
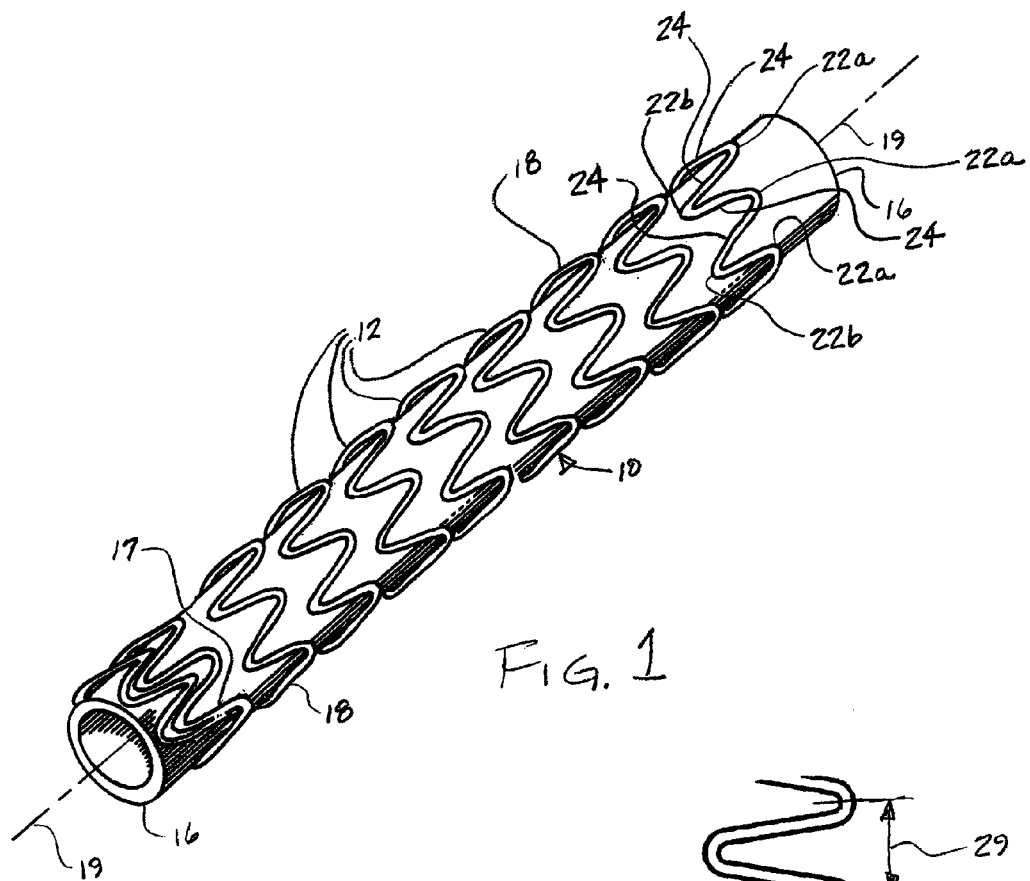
FIG. 1 shows a perspective view of a preferred stent for use with the present invention.

FIG. 1 shows a perspective view of a stent 10 that is preferred for use with the present invention. The stent 10 shown comprises a helical winding of a length of serpentine wire 18. Sequential windings of the helical wound serpentine wire 18 result in spaced-apart adjacent stent elements 12. The ends 17 of wire 18 may be secured by any suitable method (e.g., welding) to the adjacent helical winding. For clarity, stent 10 is shown with a mandrel 16 extending through and beyond both ends of the stent lumen, making the side closest to the viewer visually apparent while blocking the view of the side of stent 10 furthest from the viewer. Mandrel 16 is present only for clarity of visualization and is not a part of stent 10.

The helically wound serpentine wire 18 extends continuously between opposing ends of stent 10, wherein opposing apices 22a and 22b formed of wire bends of relatively small radii are interconnected by straight or relatively straight wire segments 24. The apices typically "point" in directions that are substantially parallel to the longitudinal axis 19 of the tubular form of the stent 10, with alternating apices 22a and 22b pointing in opposite directions, that is, pointing to opposite ends of the stent. As shown by FIG. 1, it is preferred that apices pointing in one direction (e.g., apices 22a) are aligned along a first common line while the apices pointing in the opposite direction (e.g., apices 22b) are aligned along a second common line.

Figure 1A:
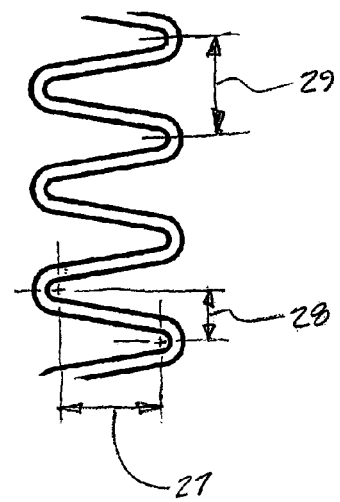
FIG. 1A shows a plan view of details of serpentine wire forms described by FIG. 1.

FIG. 1A shows a plan view of details of serpentine wire forms described by FIG. 1; dimensions relate to Example 1 described below. Dimension 27 is considered as the height of adjacent opposing apices while dimension 28 is the width of adjacent opposing apices. Dimension 29 describes one full period of the serpentine form.

Figure 2:
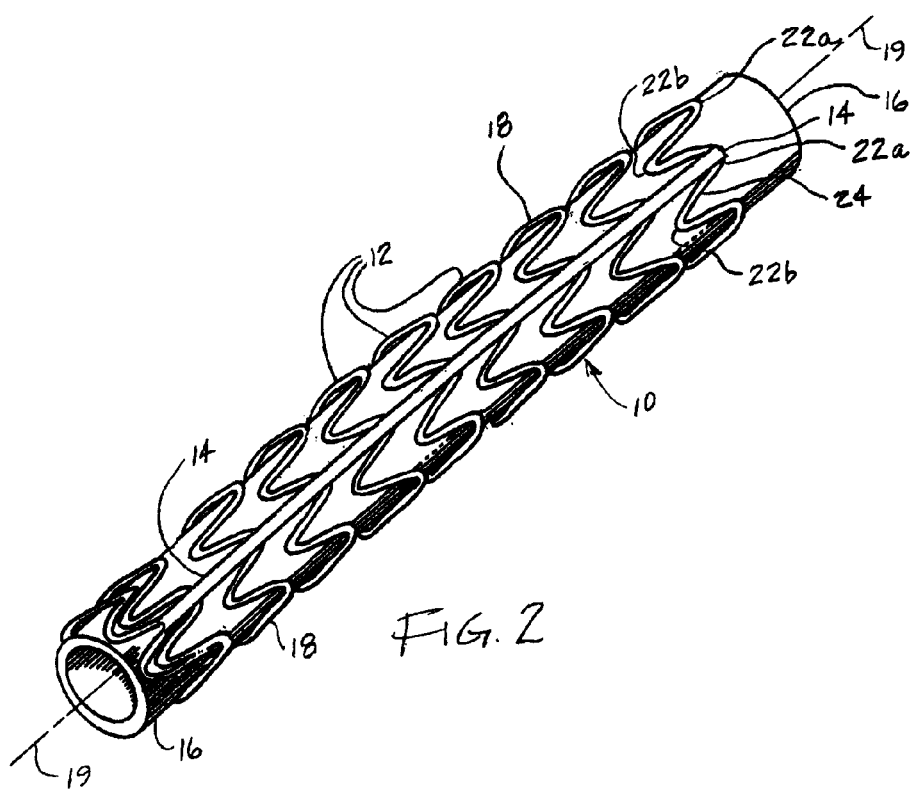
FIG. 2 describes a perspective view of an open-frame stent wherein spaced-apart, adjacent stent elements are interconnected by a flexible strip of implantable material.

FIG. 2 describes a perspective view of an open-frame stent 10 wherein spaced-apart, adjacent stent elements 12 are interconnected by a flexible strip 14 of implantable material. Adjacent stent elements 12 may be individual ring-shaped elements or alternatively adjacent windings of a continuous helically wound wire. The use of connecting strips 14 provides the resulting stent with good flexibility and good axial strength while maintaining the spacing of the adjacent stent elements 12.

Connecting strips 14 are preferably polymeric, and may be made from a variety of implantable polymeric materials including bioabsorbable polymers. Bioabsorbable polymers particularly lend themselves to the construction of stents having flexibly connected stent elements wherein the stent may be removed (particularly a helically wound stent) after degradation of the bioabsorbable connecting elements. ePTFE strips (porous expanded PTFE) made from ePTFE films are particularly preferred for their strength, flexibility and biocompatibility.

Strips may extend for less than the entire length of the stent if appropriate. If more than one strip is used, the individual strips may have different lengths or the same length. It is generally preferred, however, that all strips extend for the full length of the stent.

Strips 14 are joined to stent 10 at points where they are in mutual contact. It is preferred that all such contact points are attached. Preferably they are attached by the use of suitable adhesives or by melt-bonding of the strip polymer. Various biocompatible adhesives may be used, including melt-bondable thermoplastics.

For ePTFE strips made from ePTFE films, a preferred adhesive is a continuous coating of a thermoplastic fluoropolymer, particularly fluorinated ethylene propylene (FEP). The FEP coating may be applied to the ePTFE film by a process which comprises the steps of:

a) contacting one side of the ePTFE film with a layer of FEP film (or another alternative thermoplastic polymer if so desired);
b) heating the composition obtained in step a) to a temperature above the melting point of the thermoplastic polymer;
c) stretching the heated composition of step b) while maintaining the temperature above the melting point of the thermoplastic polymer; and
d) cooling the product of step c).

The thermoplastic film coating applied to the ePTFE film by this method may be either continuous (non-porous) or discontinuous (porous). If discontinuous, the process may be adjusted to achieve the desired degree of porosity to include a coated film that is as porous as the precursor ePTFE film. The coated film used for the present invention is most preferably a continuously (non-porous or substantially non-porous) coated film.

Figures 2A, 2B, 2C, 2D:
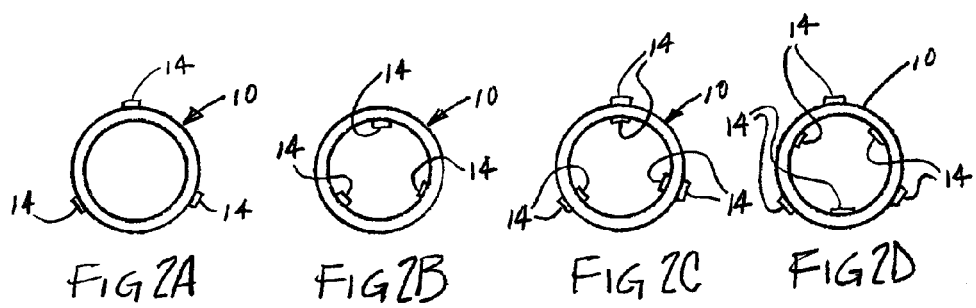
FIGS. 2A-2D are transverse cross sectional views that show various relationships between connecting strips and stent elements.

While a single strip 14 may be used along only one side of the stent 10, oriented in a direction substantially parallel to the longitudinal axis of the stent, multiple (at least two) such strips are preferred, with the strips preferably being equally spaced radially about the stent. Three connecting strips 14 are preferred to achieve uniform bending properties, as shown by the transverse cross section of FIG. 2A. Ideally these are spaced equidistant radially (120° apart) around the circumference of the stent, although some variability of this spacing has not been seen to be particularly detrimental to bending properties. Strips 14 are shown attached to the outer surface of stent 10. Alternatively, strips 14 may be attached to the inner surface of stent 10 (FIG. 2B) or to both the inner and outer stent surfaces (FIGS. 2C and 2D).

Figure 2E:
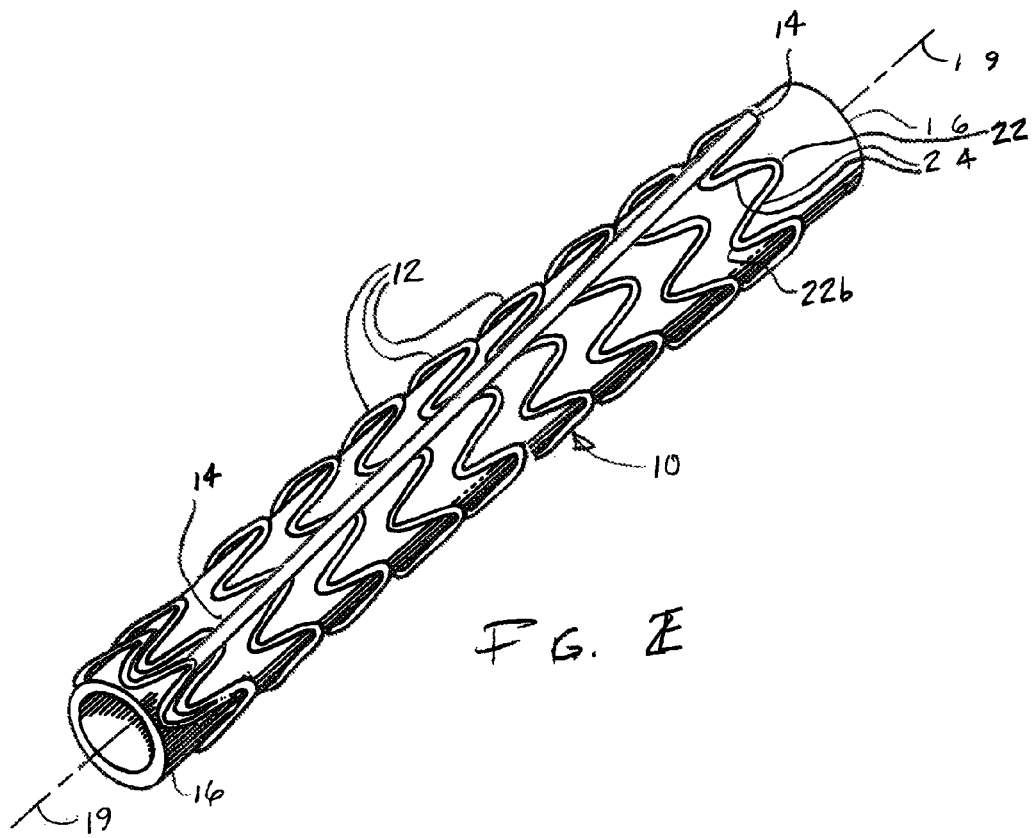
FIG. 2E is a perspective view showing that a connecting strip may have a slight helical orientation while still being substantially longitudinally oriented.

As shown by FIG. 2E, strip 14 may have a slight helical orientation while still being substantially longitudinally oriented, although orientations parallel to the longitudinal axis are preferred.

Figure 2F:
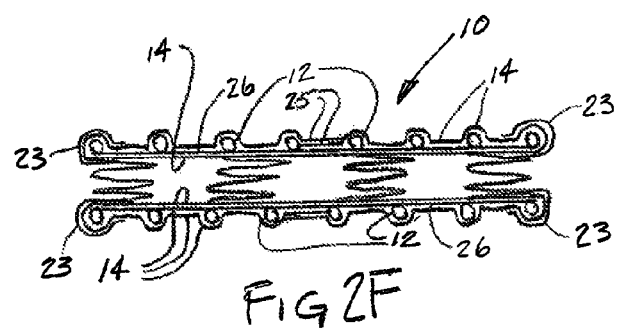
FIG. 2F shows a longitudinal cross section of a stent provided with two longitudinally oriented strips placed 180° apart.

FIG. 2F shows a longitudinal cross section of a stent 10 provided with two strips 14 placed 180° apart, with the section being taken through each of the two strips 14. This figure shows how each strip 14 is placed on the inner surface of stent 10, with ends of the strip 14 extending beyond the ends of the stent. The strip 14 in this embodiment is in excess of twice the length of the finished stent 10, allowing the ends of strip 14 to be wrapped back over and attached to the outer surfaces of the stent elements 12, with the extreme ends of strip 14 overlapping and attached to each other (reference 25). As well as strips 14 being attached (bonded) to their points of contact with stent elements 12, they are attached to each other between adjacent stent elements as shown (reference no. 26). The ends of the stent 10 may optionally be provided with a circumferentially applied tape covering 23 that aids in securing the extreme wire ends of the wire stent.

A self-expanding stent was made using nitinol wire of round cross section and of 0.15 mm diameter. The wire was wound into the helically wound serpentine form (shown in FIG. 1) on a manufacturing mandrel having a series of pins protruding from its external surface at specific points. The resulting serpentine form had apices of about 0.3 mm radius (measured from the center point of the bend to the surface of the wire closest to the center point of the bend). The height of adjacent opposing apices was about 1.6 mm (dimension 27 in FIG. 1A) while the width of adjacent opposing apices was about 2.3 mm. The resulting stent incorporated eight full periods of the serpentine pattern for each full revolution of the serpentine wire about the stent circumference. The stent was of about 6 mm inside diameter, having been manufactured to its fully deployed diameter at which the connecting strips were to be attached. The completed stent may subsequently be compacted to a smaller diameter for insertion into a vasculature by various known means including iris type compaction devices or by pulling the stent through funnel devices.

Following forming of the nitinol wire into the helically wound stent, the finished wire form, while still on the manufacturing mandrel, was then placed into a convection oven set at 450° C. for 9 minutes for heat treating, and removed from the oven and allowed to cool to ambient temperature. The stent was then removed from the mandrel.

Connecting strips for this 5 cm long stent were 1.0 mm wide, 11 cm long strips of ePTFE film of about 0.012 mm thickness subsequently provided with a continuous (substantially non-porous) FEP coating. The ePTFE used to make these strips was of about 0.5 g/cc density and of about 50 micron average fibril length. The coated strip was of about 0.05 mm thickness. Break strength for these strips was 0.5 kg or greater.

Average fibril length of the ePTFE film was estimated from scanning electron photomicrographs of the surface of the film. Film thickness measurements are preferably made (including for the determination of bulk volumes for density values) by placing a sample between the pads of a Mitutoyo model no. 804-10 snap gauge having a part no. 7300 frame and gently easing the pads into contact with the opposing surfaces of the sample under the full force of the spring-driven snap gauge pads.

Three strips were used to create the stent, spaced apart radially. Each of the three strips was aligned longitudinally (parallel to the longitudinal axis of the stent) with and covering a row of wire apices pointing at the same end of the stent. Arrangement of the strips was such that between two strips was one row of uncovered apices pointing in the same direction as the rows covered by the two strips. The other two spaces between the connecting strips each had two rows of uncovered apices pointing in the same direction as the covered apices.

The stent having substantially longitudinally oriented connecting strips was manufactured using the helically wound wire stent and FEP coated ePTFE connecting strips described above. The manufacturing process involved fitting a sacrificial 5 mm inside diameter, longitudinally extruded and expanded ePTFE tube onto a porous metal 5 mm diameter stainless steel mandrel. Two circumferential wraps of 6 mm wide FEP coated ePTFE film were applied over the surface of the sacrificial tube with the FEP facing away from the sacrificial tube. These two wraps were located about 4.4 cm apart. Three of the 11 cm long FEP coated strips were laid lengthwise along the surface of the sacrificial ePTFE tube with their FEP coated surface facing away from the sacrificial tube. These strips were spaced approximately 120° apart circumferentially. The ends of the strips were temporarily secured to the mandrel with ePTFE tape. The helically wound 5 cm long serpentine wire stent was then fitted over the assembly with the stent ends centered on each circumferential wrap of 6 mm wide ePTFE film. Care was taken to see that the adjacent helical stent windings were spaced apart equal distances. After removing the temporary ePTFE tape, the radial position of each of the three ePTFE connecting strips was then adjusted with respect to the stent so that each strip was located along a row of stent apices pointed in the same direction for all three strips.

For each strip, both ends were laid back over the outer surface of the stent in line with the portion of the strip beneath the stent, with about 0.5 cm of the very ends of both strips overlapping as shown by reference no. 25 in FIG. 2F. The strips were secured in this position with a temporary wrapping of 0.012 mm thick polyimide film. Each stent end was then given a circumferential wrapping with a narrow gold marker band (e.g., 0.0625 mm by 0.025 mm) and an outer circumferential wrapping of another layer of 6 mm wide FEP coated ePTFE film, this time with the FEP facing inward. The entire assembly was wrapped in polyimide film and placed into a convection oven set at 320° C. for 10 minutes with a vacuum applied to the porous metal mandrel. After removal from the oven and being allowed to cool to about ambient temperature, the polyimide film was removed. Any of the circumferentially wrapped ePTFE film covering the stent ends that protruded beyond the ends of the wire stent was trimmed off with a scalpel.

The three ePTFE connecting strips were well adhered to the stent and to themselves between the stent elements (reference no. 26, FIG. 2F). The resulting stent had a porosity index of about 82%. It demonstrated good flexibility and kink resistance in bending. The stent was able to be bent to an inside bend radius of 3 mm without kinking.

The same stent made with a single connecting strip of the same dimensions would have a porosity index of 93%

A second fundamental embodiment uses a flexible, preferably polymeric filament laced along the length of the stent to locate the adjacent stent elements (e.g., adjacent helical windings) with respect to each other. Stent elements include serpentine wire or machined elements having repeating sinusoids with apices connecting relatively straight segments. The stent elements may be individual rings or may be adjacent windings of a helically wound serpentine wire, or may be any other stent form having spaced apart elements that lend themselves to being connected by a filament. Alternate apices of the serpentine form point in opposite directions, i.e., toward opposite ends of the stent. The filament may be of a variety of polymers including PET, polyurethane, PTFE, etc. Porous expanded PTFE fibers are preferred because of their strength, flexibility and biocompatibility. The filaments may optionally be provided with coatings of adhesives (including heat-activated adhesives) to allow bonding to stent elements. The filaments may also be a bioabsorbable polymer such as PGA, PLA, PGA/PLA, PGA/TMC, etc. The use of a bioabsorbable filament is possible in that, once deployed at a desired site in a body conduit, the interference of the deployed stent elements with the luminal surface of the body conduit will hold the stent in place with the elements properly spaced apart for most implant applications.

The filament is substantially longitudinally oriented (along the length of the stent) as it connects adjacent, spaced-apart stent elements, meaning that the predominant orientation of the filament, represented by a straight line (neglecting the curvature of the exterior surface of the stent, i.e., as if the stent form were considered in a flattened, plan view) laid over the filament between the ends of the stent, is substantially longitudinally oriented. This line is considered substantially longitudinally oriented if it is parallel to the longitudinal axis of the stent, plus or minus 45°. Most preferred orientations are parallel to the longitudinal axis, or very close to parallel (plus or minus 5°). As shown by the schematic plan view of FIG. 3A, the filament is preferably laced so that it includes a transversely oriented loop around one half of a full period of the serpentine wire, with these loops created around sequential periods of the serpentine form that lie along the length of the stent in axial alignment. One or more of these filament lacings may be provided along the length of the stent. When more than one lacing filament is used, they are spaced apart in equal radial amounts (e.g., if three lacing filaments are used along the length of the stent, they are spaced 120° apart). The use of three filaments offers a particularly good combination of stent flexibility and strength.

Figure 3:
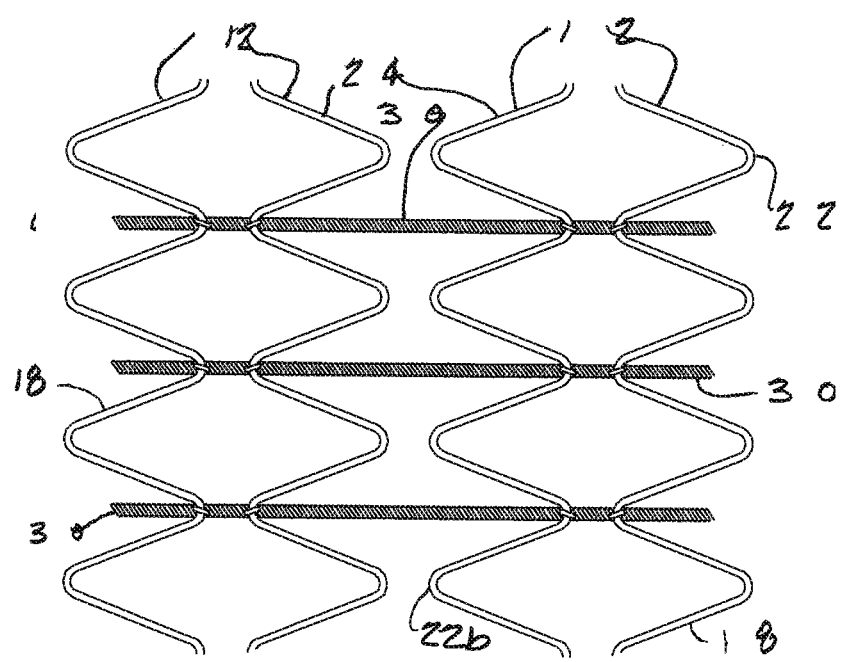
FIG. 3A is a schematic view plan view of serpentine wire segments from portions of four adjacent helically wound stent elements, showing a substantially longitudinally oriented filament interconnecting adjacent stent elements.
FIGS. 3B and 3C are detail views of a portion of FIG. 3A showing particulars of the filament relationship with the serpentine wire stent elements.
FIG. 3D shows a schematic plan view of an alternative serpentine wire form for a stent wherein the serpentine wire may be provided with a circumferential rather than helical orientation, and with stent elements interconnected by a substantially longitudinally oriented filament.
FIG. 3E is a detail view of a portion of FIG. 3D.
FIG. 3F shows the same stent form as FIG. 3D with an alternative arrangement of the interconnecting filament.
FIG. 3G shows an alternative stent form to that of FIG. 3F with the same filament arrangement.
FIG. 3H shows an alternative arrangement of the substantially longitudinally oriented interconnecting filament.
FIG. 3I is a detail view of a portion of FIG. 3H.
FIG. 3J shows an alternative arrangement of the substantially longitudinally oriented interconnecting filament.
FIG. 3K is a detail view of a portion of FIG. 3J.
FIGS. 3L-3N show examples of filament arrangements that may be used with opposing apices.
Figure 3A:
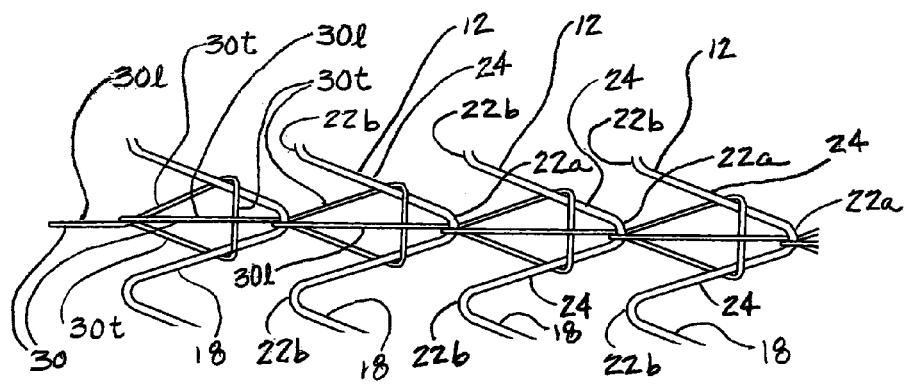

FIG. 3A is a schematic view plan view of serpentine wire segments from portions of four adjacent helically wound stent elements 12 incorporating opposing apices 22a and 22b connected by straight segments 24. These spaced-apart stent elements 12 are interconnected by filament 30 extending between both ends (not shown) of stent 10. Filament 30 is laced through stent elements in the fashion shown so that it includes longitudinal segments 30l and transverse loop segments 30t. This form of lacing provides very good stent flexibility and axial strength while allowing a degree of length variability in that the application of tension to the length of the stent results in a slight amount of length extension. The pattern of the lacing shown is best followed by examination of the close-up details of FIGS. 3B and 3C, with arrows 30a, 30b and 30c showing the lacing accomplished in that respective sequence.

Figure 3B:
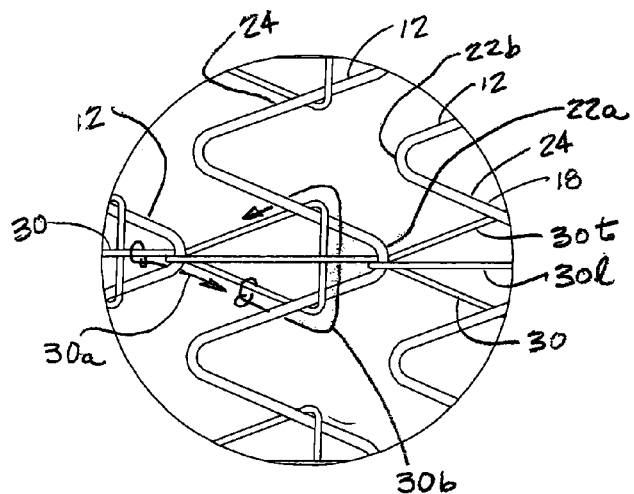
Figure 3C:
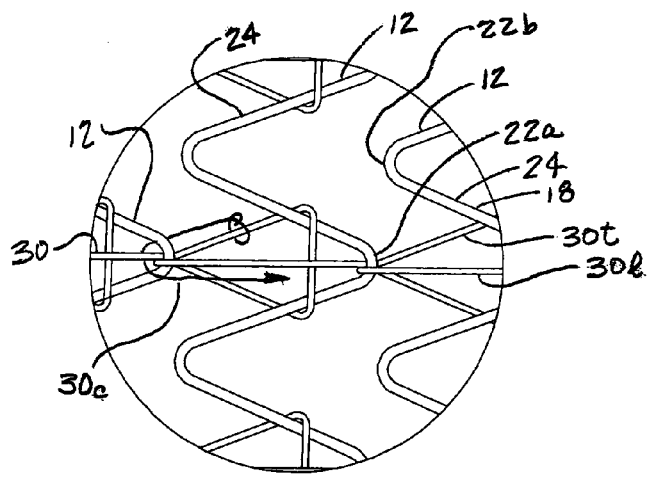
Figure 3D:
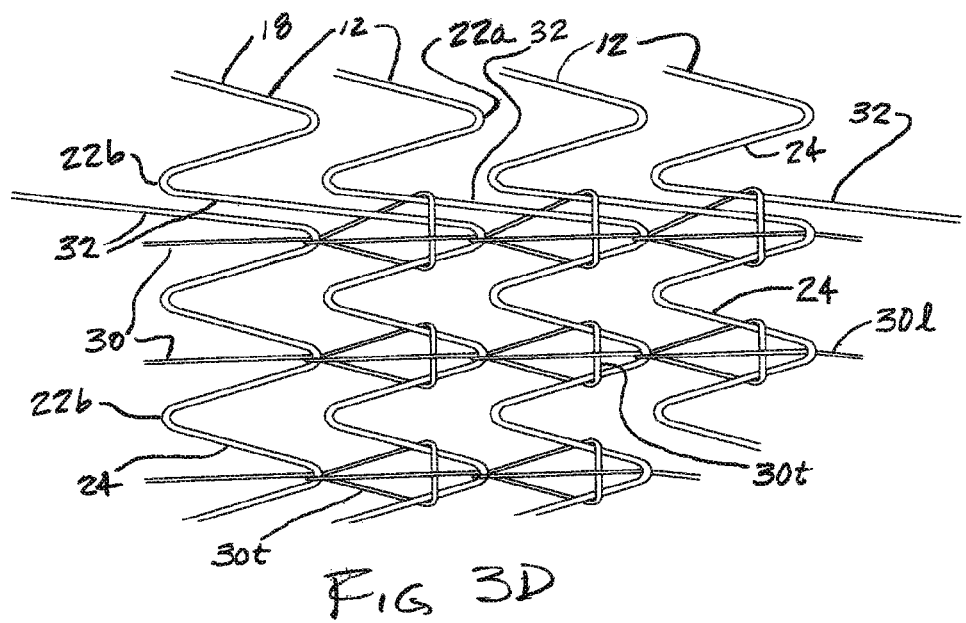
Figure 3E:
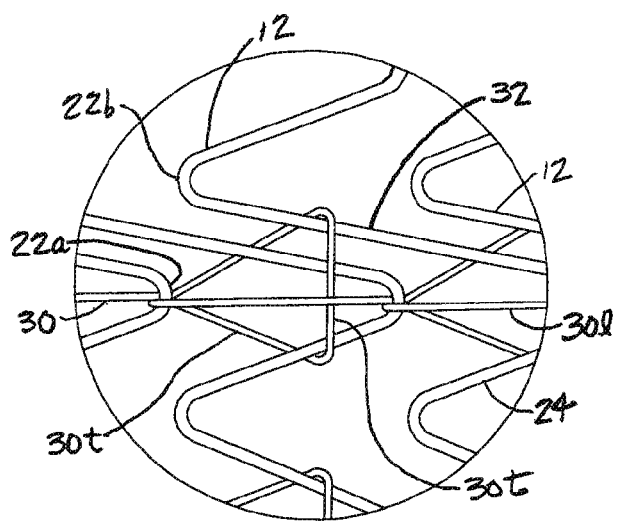

FIG. 3D shows a schematic plan view of an alternative to the helically wound wire stent of (for example) FIGS. 1 and 3A. The sinusoids shown in FIG. 3D include opposing apices 22a and 22b connected by straight segments 24 in the fashion shown previously for the helically wound constructions. The stent portion shown in FIG. 3D differs in that, once per revolution, straight segment 24 is replaced by a longer straight segment 32 that connects one winding (or stent element) 12 to the adjacent winding (or stent element) 12. This use of the longer straight segments 32 allows the individual windings 12 to be circumferentially oriented (perpendicular to longitudinal axis 19) rather than helically oriented wherein the windings have a pitch that is less than perpendicular to the longitudinal axis 19. This stent arrangement may be used with connecting strips 14 in a fashion similar to that shown in FIG. 2, and for other embodiments as will be subsequently described. FIG. 3D and the detail of FIG. 3E show the transverse segment of the lacing filament 30t to extend around the adjacent air of longer straight segments 32 as well as one adjacent straight segment 24 of conventional length. Any other filaments extending between ends of the stent (e.g., two other filaments if a total of three are used) are laced in the fashion shown by FIG. 3A-3C.

Figure 3F:
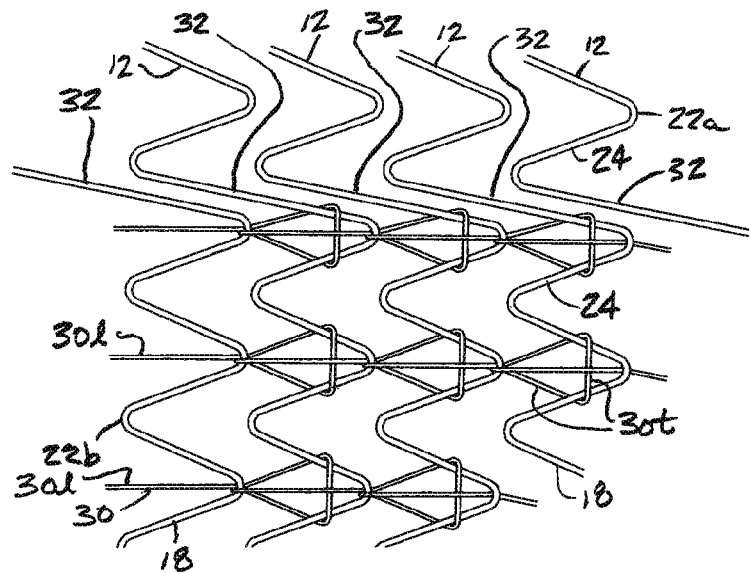

Alternatively, as shown by FIG. 3F, the transverse loop 30t may be fitted only around one longer straight segment 32 and the adjacent straight segment 24 of conventional length, thereby passing between the adjacent long straight segments 32.

Figure 3G:
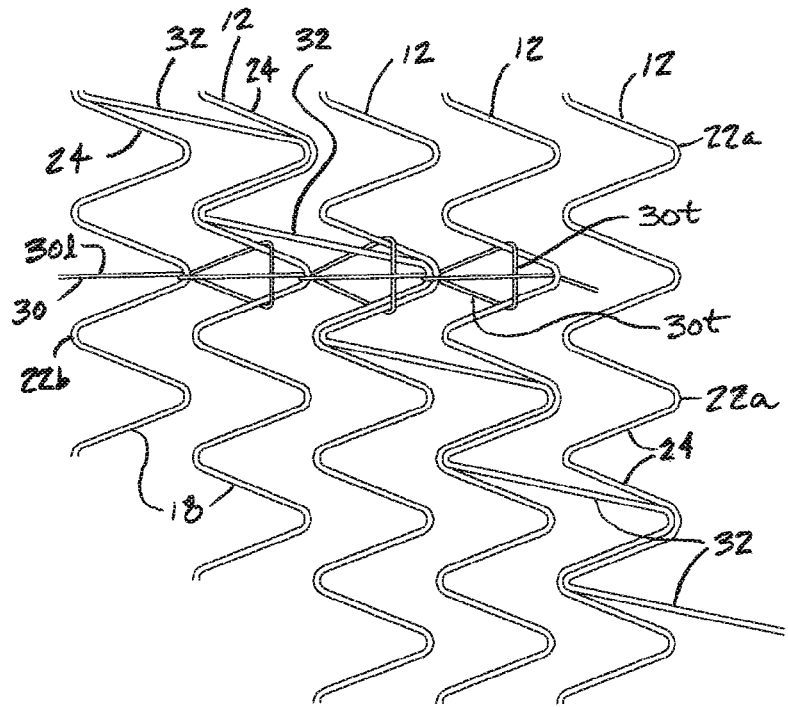

FIG. 3G shows a similar stent structure to that of Figure F, differing primarily in that the long straight segments 32 are offset by one period of the serpentine form per each circumferential revolution. The filament lacing pattern is the same.

An additional advantage of the lacing patterns shown in FIGS. 3A-3G is that manufacture of these patterns may be easily automated.

Figure 3H:
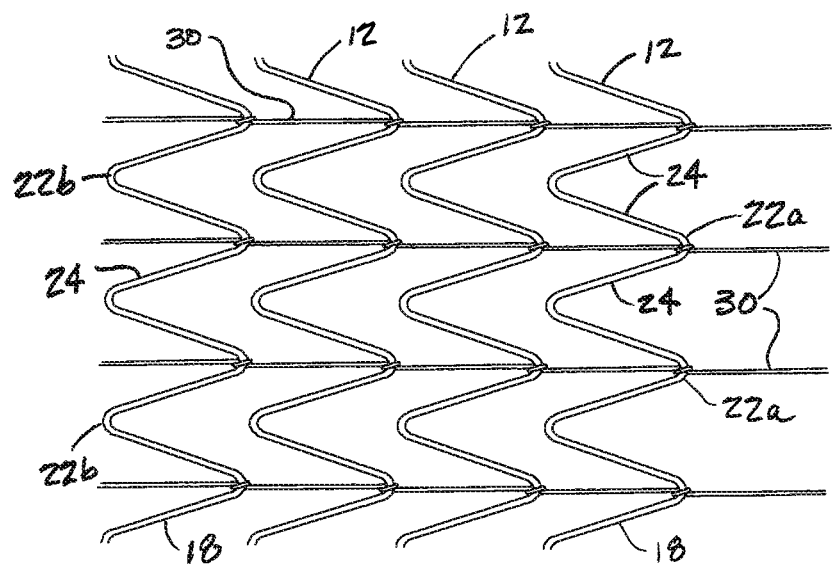
Figure 3:
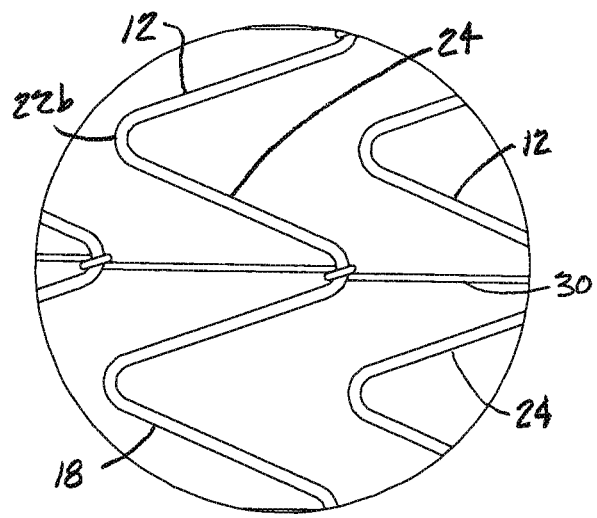
Figure 3J:
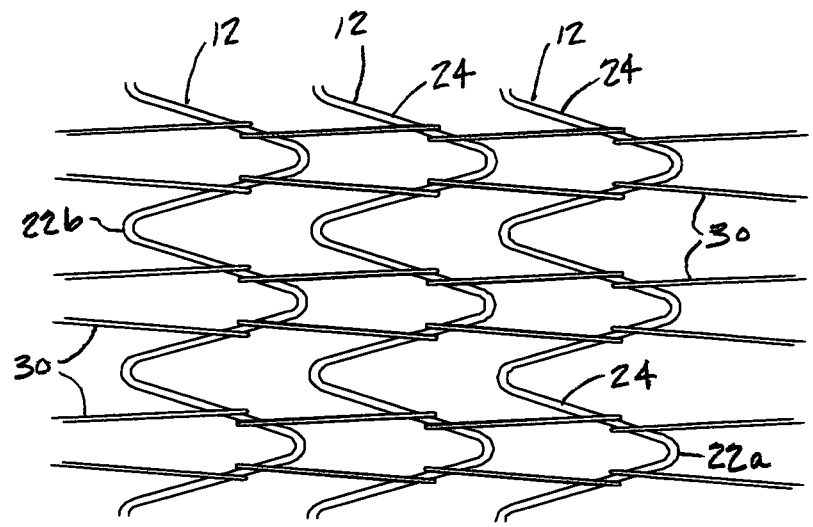
Figure 3K:
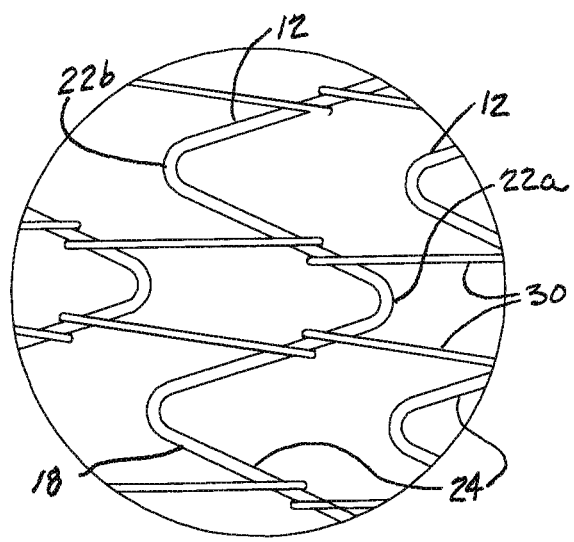
Figure 3L:
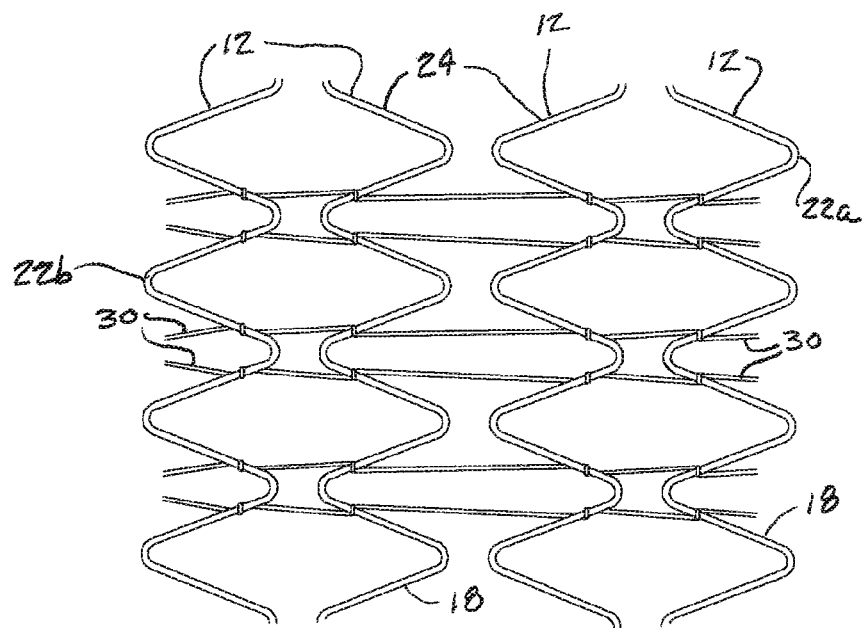
Figure 3M:
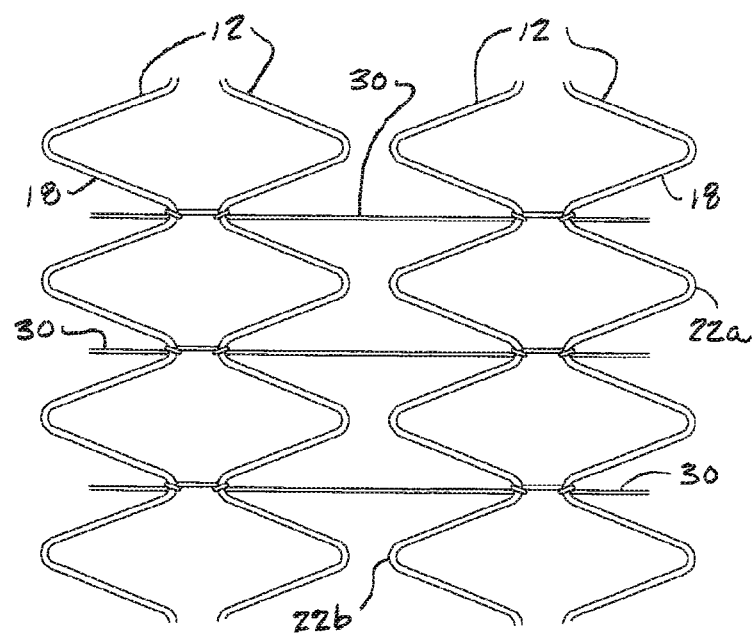

Other lacing techniques are also possible, such as those shown by FIG. 3H and associated detail FIG. 3I, and FIG. 3J and associated detail FIG. 3K. FIGS. 3L-3N show examples of how the lacing techniques may be applied to stents having opposing apices. FIG. 3N shows an embodiment wherein two or more filaments are twisted together, capturing the stent element as the twisting proceeds.

It is apparent that a variety of substantially longitudinally oriented filament lacing methods may be used with various stent forms having spaced-apart stent elements, each method having advantages. For example, substantially longitudinally oriented patterns that also incorporate transverse filament lacing aspects (for example, of the type described by FIG. 3A) can be used to affect torsional properties of the stent.

As noted above, the chosen filaments may be provided with adhesives if desired for attachment of contact points of the filaments to the stent elements. While this may inhibit stent flexibility, it may be desired for other reasons such as precisely limiting the length of an expanded stent. ePTFE filaments may be provided with melt-bondable coatings of polymers having lower melt temperatures than PTFE; fluorinated ethylene propylene (FEP) is an example. Such a coating may be applied by various methods including extrusion over the filament, powder coating of the filament with powdered FEP that is subsequently melted to flow over the filament surface, or running the filament through a bath of molten FEP optionally followed by pulling the filament through a die to achieve uniformity of the coating. Alternatively, the stent may be provided with a coating of adhesive such as by powder coating with FEP. ePTFE filaments may be made by rolling ePTFE films (see, for example, U.S. Pat. No. 5,288,552 to Hollenbaugh et al.). The films used to create filaments may be FEP coated films of the type described previously.

An example of a 6 mm expanded diameter nitinol wire stent having adjacent elements connected by filaments was created using the same type of helically wound serpentine wire stent as created for Example 1. The filament chosen was an ePTFE filament provided with a coating of FEP melt-bondable adhesive. The filament had a diameter of 0.1 mm, a tensile strength of 620 grams and a weight per unit length of 0.018 grams/meter. Eight filaments were laced into the stent, connecting the adjacent stent elements as shown by FIGS. 3A-3C, with one filament laced into each row of apices that pointed at one end of the stent. The resulting stent exhibited excellent flexibility, being able to be bent to an inside bend radius of almost zero without kinking. Porosity index for this stent was 97%.

A third fundamental embodiment is a stent provided with a perforated covering of a thin, strong and flexible, preferably polymeric graft material, in the form of a sheet of material rolled and preferably seamed to form a tube, or alternatively as a seamless integral tube, that is provided with a multiplicity of perforations or apertures. The graft material is thus integral or monolithic as opposed to being created from separate filaments or threads with multiple crossover points that add to thickness and may be vulnerable to breakage and consequent unraveling of the covering. Various implantable polymeric materials may be used for the perforated cover including PTFE, PET, polyurethane, silicone, fluoroelastomers and bioabsorbable polymers.

Figure 4A:
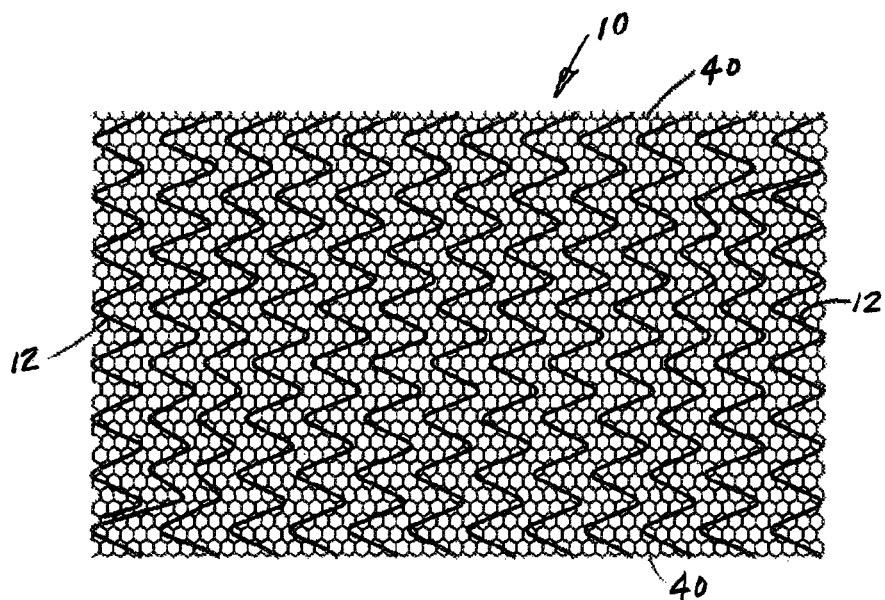
FIG. 4A is a plan view of a helically wound serpentine wire stent provided with a hexagonally perforated graft covering, as it would appear if the tubular form of the stent was cut along its length and laid out flat.

FIG. 4A is a plan view of a helically wound serpentine wire stent 10 provided with a perforated graft covering 40, as it would appear if the tubular form of the stent was cut along its length (parallel to the longitudinal axis) and laid out flat. The stent is the same type as shown in FIG. 1. The hexagonally perforated covering 40 is a preferred covering offering good flexibility and strength when made as described below.

Figure 4B:
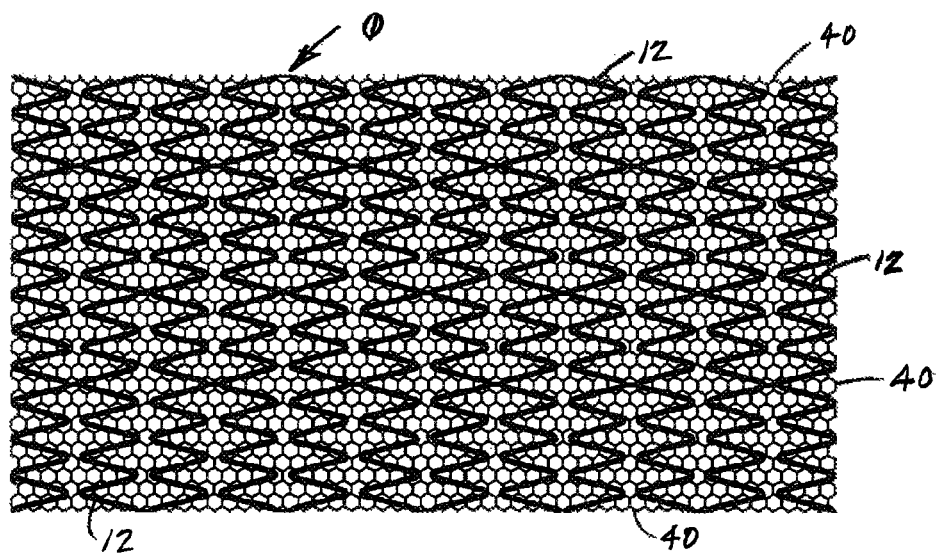
FIG. 4B is a plan view of a series of individual serpentine stent rings, arranged with the direction of the apices opposing each other rather than aligned in the same direction as shown in FIG. 4A, provided with a hexagonally perforated cover.

FIG. 4B is a similar plan view of a series of individual serpentine stent rings 12 wherein two rings per row are connected by stent elements, arranged with the direction of the apices opposing each other rather than aligned in the same direction as shown in FIG. 4A; the stent of FIG. 4B uses the same hexagonally perforated graft covering 40 as the stent of FIG. 4A.

Figure 4C:
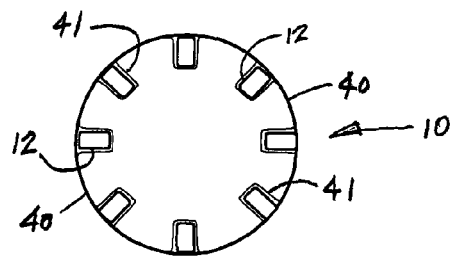
FIG. 4C is a transverse cross section of a stent 10 provided with the perforated covering 40.

FIG. 4C is a transverse cross section of a stent 10 provided with the perforated covering 40. The stent elements 12 shown are of wire having a rectangular cross section. Stent elements 12 are provided with a coating of an adhesive 41 such as a melt-bondable FEP applied to the stent elements 12 by powder coating.

FIGS. 4D-4G describe plan views of alternative perforated coverings having different hole patterns. While hexagonal perforations are preferred, the other perforation patterns such as rectangular, circular, triangular and square may be desirable for certain applications. It is also apparent that, for perforation patterns that are not perfectly symmetrical within the plane of the covering, that the covering sheet may be oriented as desired with respect to the length of the stent. Perforations may be made to desired sizes, with aperture size being defined herein as the diameter of the largest inscribed circle that may be fitted into the opening. It is further apparent that different size openings may be provided within the same covering. The total opening area and the amount of web material between openings may be selected to provide the desired porosity index.

Figure 4D:
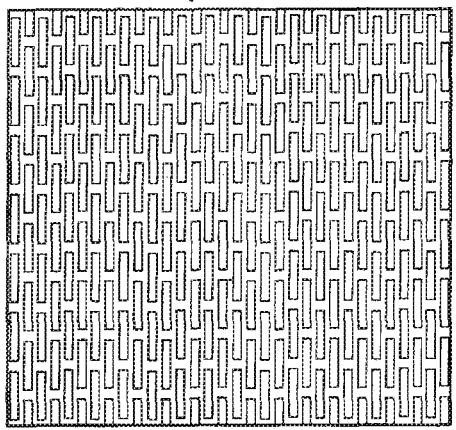
FIGS. 4D-4G describe plan views of alternative perforated coverings having alternatively shaped perforations.
Figure 4E:
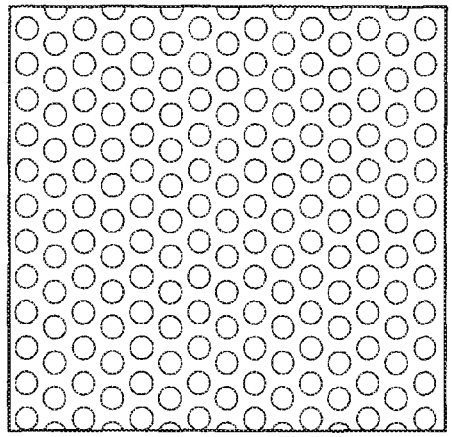
Figure 4F:
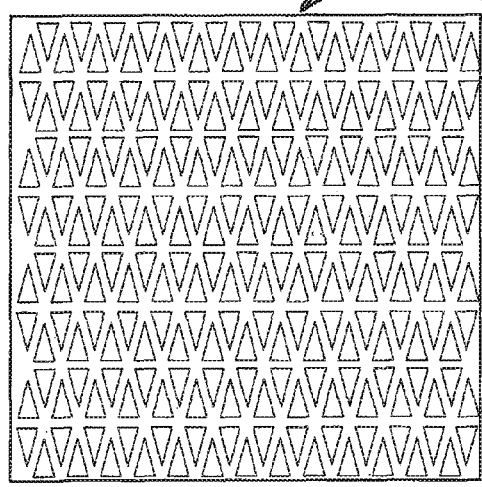
Figure 4G:
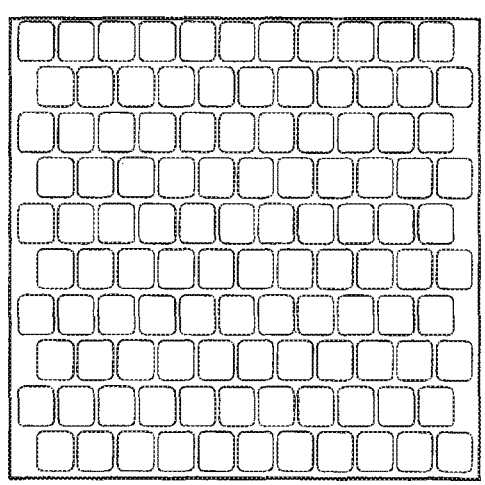

The rectangular patterns of FIG. 4D may also be made by using slits through the material. Either the rectangular or slit pattern may be usefully oriented with the long dimensions of the slits or rectangles parallel to the longitudinal axis of the stent. Openings of this type may allow the covering to be attached to a stent in a partially or fully compacted state, wherein, upon expansion of the stent, the slit or rectangle deforms into a larger generally hexagonally shaped aperture.

Figure 4H:
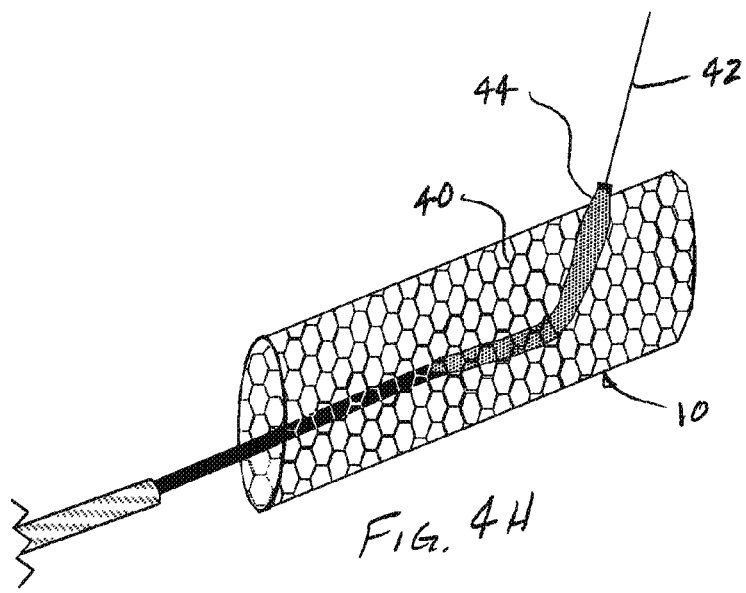
FIG. 4H is a perspective view of a stent provided with a perforated cover shown as it would appear deployed in vivo, located in a vessel at a site where the stent crosses a side vessel and with a balloon introduced through a cover perforation and extending into the side vessel.

FIG. 4H is a perspective view of a stent 10 provided with a perforated cover 40 shown as it would appear deployed in vivo, located in a vessel at a site where the stent 10 crosses a side vessel (not shown). A guidewire 42 is introduced through a perforation aligned with the entrance to the side vessel, after which a balloon catheter is introduced over the guidewire directing the balloon 44 through the same perforation. The balloon 44 may subsequently be inflated to rupture the perforation and create an enlarged transmural opening through the perforated graft cover aligned with the entrance to the side vessel.

Figures 4I, 4J:
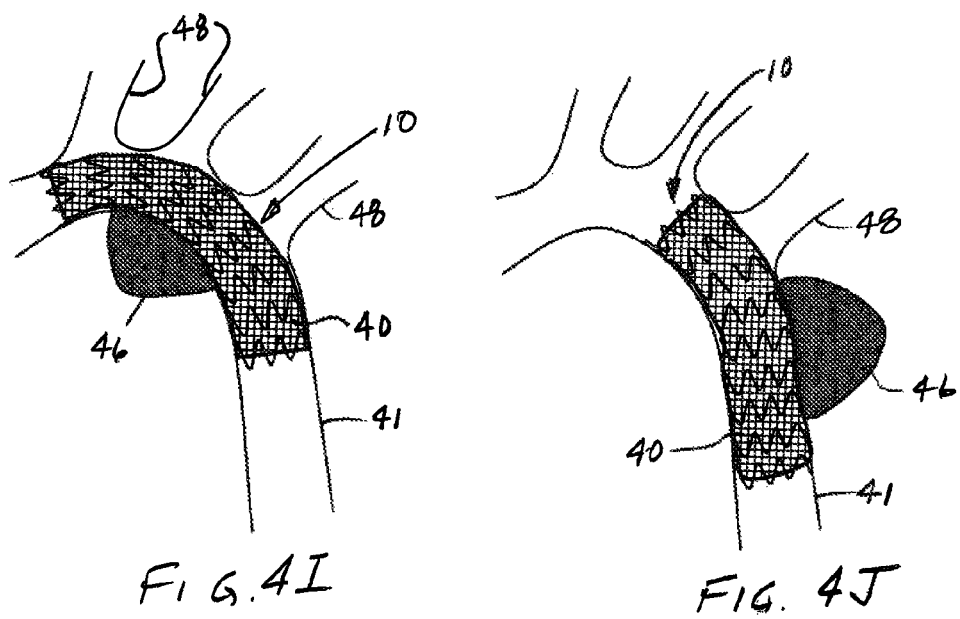
FIGS. 4I and 4J show stents provided with perforated coverings placed over thoracic aneurisms.

FIGS. 4I and 4J show stents 10 provided with perforated coverings 40 implanted into blood vessels 41 over thoracic aneurisms 46. The aneurisms 46 may be filled with a suitable gel or other biocompatible material that is held in place by perforated cover 40 while blood flow is provided through the lumen of the stent 10. Blood flow is also maintained into side branch vessels 48 through the perforated cover 40.

Figure 4K:
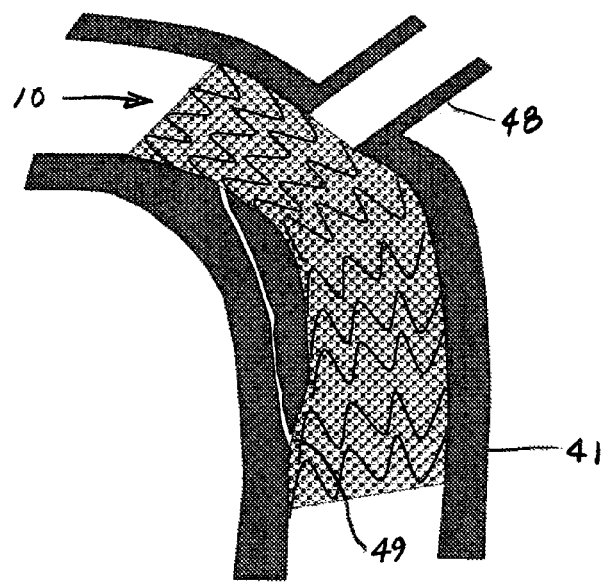
FIG. 4K shows a stent provided with a perforated cover used to repair a dissection in a blood vessel.

FIG. 4K shows how a stent 10 provided with a perforated cover 40 may be used to repair a dissection 49 in a blood vessel 41.

Figure 4L:
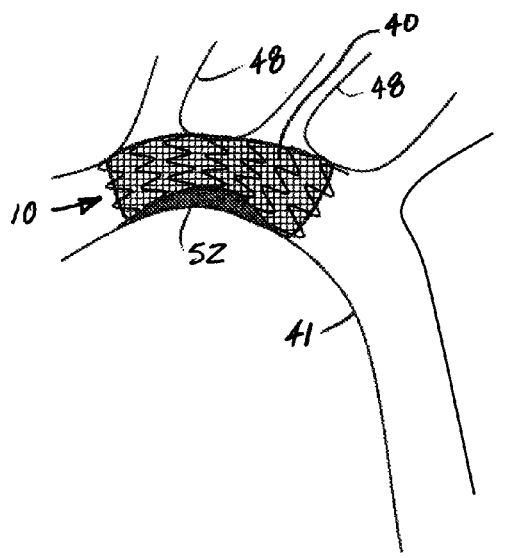
FIG. 4L shows a stent provided with a perforated cover used to hold plaque against a vessel wall while still allowing flow through an adjacent side branch vessel.

FIG. 4L shows a stent 10 provided with a perforated cover 40 used to hold plaque 52 against a vessel wall while still allowing flow through an adjacent side branch vessel.

Figure 4M:
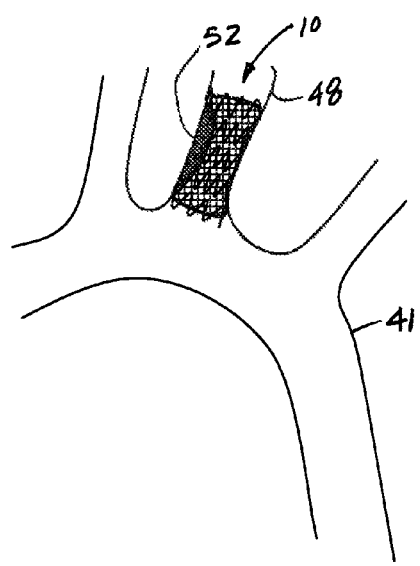
FIG. 4M shows a stent provided with a perforated cover used to hold plaque or emboli contained against the wall of a small blood vessel.

FIG. 4M shows a stent 10 provided with a perforated cover 40 used to hold plaque or emboli 52 contained against the wall of a small blood vessel 48.

Figures 4N, 4P:
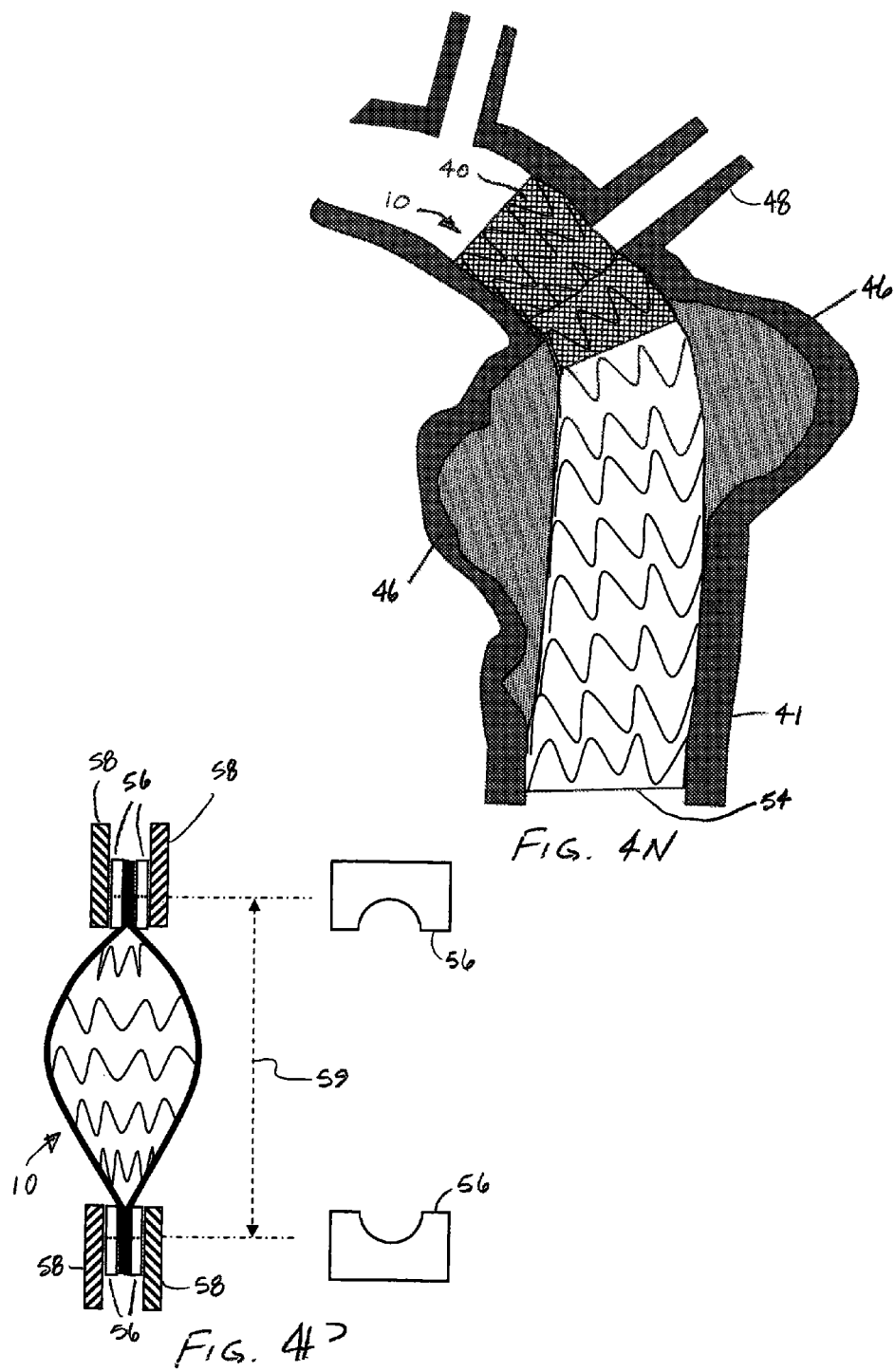
FIG. 4N shows a stent provided with a perforated cover located distally to a stent-graft located to repair an aneurysm wherein the perforated cover stent aids in anchoring the stent-graft near a branch vessel while allowing flow through the branch vessel.
FIG. 4P is a schematic side view of a stent tensile test configuration.

FIG. 4N shows a stent 10 provided with a perforated cover 40 located distally to a stent-graft 54 located to repair an aneurysm wherein the perforated cover stent aids in anchoring the stent-graft near a branch vessel while allowing flow through the branch vessel. The aneurisms may optionally be filled with coils, a suitable gel or other biocompatible material.

FIG. 4P is a schematic side view of a stent tensile test configuration.

Perforated covers were created by initially wrapping several layers of an ePTFE film that includes a discontinuous (porous) layer of FEP. Films made as taught by U.S. Pat. No. 5,476,589 to Bacino are suitable for FEP coating and use in this application. The film used ranged from 2.5 to 5 microns in thickness and had a density range of about 0.5 to 1.0 g/cc. The film was wrapped circumferentially, with the FEP side oriented outwards, onto a glass mandrel approximately 1 mm diameter larger than the outside stent diameter. Other materials, including biocompatible polymers and metals could be used for the perforated cover structure, with process parameters adjusted accordingly. Twelve layers of the film were wrapped around the mandrel surface, with a range of 2 to 100 layers considered desirable. The wrapped mandrel was placed in a convection oven set at 320° C. for 12 minutes, and then allowed to cool to about ambient temperature.

While the perforations may be formed by various methods including the use of, for example, mechanical punches, laser cutting is preferred for speed and precision.

For cutting the perforations, the wrapped mandrel was set up on a computer controlled laser cutting tool that utilizes a beam with a wavelength of 10.6 μm (Keyence ML-G9310, Woodcliff Lake N.J.). Shorter wavelengths lasers have been tried (e.g., 157 nm wavelength laser) with the cut quality being higher (straighter cuts with less thermally effected zone as evidenced by less material retraction when visually inspecting scanning electron microscope images). The laser was programmed to cut hexagonal apertures with side length of 0.15 mm. Adjacent hexagons were offset in honeycomb fashion to minimize the amount of material between the resulting apertures and to provide relatively uniform web widths between adjacent apertures. Accounting for the laser beam width of 50 microns, the side length of the resulting hexagonal aperture is about 0.2 mm. Depending on the intended application of the stent, the length of the cut side of the hexagons may range from 0.025 to 5 mm, with 0.1 mm to 1 mm being preferable. Other aperture shapes of widely ranging sizes may also be cut. The perforations may be made to be of uniform shape, or not. It is also anticipated that the perforations may be cut after attaching the cover to the stent.

After cutting, the wrapped mandrel was heated in a convection oven set at 370° C. for 5 minutes. This post-cutting heating step has the benefit of both improving the cut quality (i.e., smoothing the edge) and minimizing the width of the membrane between the cut hexagons. This heating process encourages retraction of polymer thereby narrowing the membrane width, and may also result in a thickness increase. For example, the difference between pre-heated to post-heated web width has been measured to change from approximately 0.20 mm to 0.075 mm.

After the heating step, the resulting perforated stent cover was stripped from the glass mandrel and inverted so the FEP that was on the outer surface became the inner surface. Optionally, radiopacity enhancements could be added to the perforated cover such as attaching gold foil segments to the cover by, for example, the use of a suitable adhesive or by locally melting the FEP (for example, with a heated soldering iron).

Following manufacture of the perforated cover, a suitable stent is obtained. The stent is preferably made of nitinol, but can be fabricated of a material such as stainless steel, cobalt chromium, or bioabsorbable materials (e.g., polyglycolic acid, or other). The stent may optionally be provided with radiopaque enhancements such as gold or platinum/iridium markers crimped, embossed, or otherwise attached to the stent frame. Various stents forms were attached to perforated covers made as described. 6 mm stents of the type used to make the strip connected and the filament connected stents were used, differing only in being of 3 cm length. 37 mm helically wound wire stents were made with eight full periods of the serpentine wire forms per circumference (reference no. 29, FIG. 1A), and the width of adjacent opposing apices (reference no. 28, FIG. 1) being equal to about 6.7 mm. The height of adjacent opposing apices (reference no. 27, FIG. 1A) being equal to about 9.5 mm. 37 mm stents were heat treated on their manufacturing mandrels in a convection oven set at 470° C. for 20 minutes. After being removed form the oven and allowed to cool to ambient temperature, the resulting stent was removed from the mandrel.

The obtained stent was powder coated with a thin layer of FEP powder. This was done by using FEP powder (Dupont FEP Fluoropolymer Resin, Product Type 5101) in a table top blender within which the stent is suspended. Other melt processable polymers could be used, included fluoroelastomers, drug eluting polymers, or other polymers. The stent was placed within the blender with FEP powder and the blender activated. The powder dispersed into the volume of the blender chamber and powder coated the stent. After approximately 3 seconds, the stent was removed, and next placed into a convection oven set at 320° C. for 5 minutes. After this time, the stent was removed and allowed to air cool.

The stent was then placed on a mandrel having an outer diameter approximately equal to the inner diameter of the stent. The mandrel was covered on its outer diameter with polyimide film. To temporarily fix the stent to the mandrel, the stent was placed in a convection oven set at 320° C. for 4 minutes.

After removal from the oven and cooling of the stent and mandrel assembly, the perforated cover structure was coaxially positioned over the stent. The perforated cover was axially tensioned over the stent, causing it to decrease in diameter and come in full contact with the outer diameter of the stent. The cover ends were temporarily fixed to length on the mandrel by ePTFE tape. A temporary layer of ePTFE film was then tightly wrapped around the assembly. The perforated cover was then placed within a convection oven set at 320° C. oven for 12 minutes. After removal from the oven and being allowed to cool to ambient temperature, the temporary film wrapping was removed and the stent and perforated cover assembly removed from the mandrel. The perforated cover was then trimmed flush with the end of the stent.

The perforated cover structure may also be attached by mechanical means such as fiber or discrete mechanical attachment points (e.g., clips, etc). The perforated cover may be on the outside of the stent elements, or it may be on the inside of the stent elements, or it may be on both.

The resulting assembly should then be inspected to ensure good adherence of the stent to the perforated cover. This final assembly can then be cooled below its martensitic temperature, crimped and loaded within a catheter delivery system for implantation into a body conduit following sterilization.

Assembling a covered stent in the preceding manner has a number of advantages. First, the radial strength of the device can be optimized independent of device flexibility and perforation size. By attaching the perforated cover structure, the axial distance separation of stent rows on the outer radius of curvature is minimized and bending is accomplished by reducing the space between the adjacent stent elements on the inner radius of curvature. This allows stents to be constructed that give more uniform support to a curved vessel.

The above-described perforated cover structure minimizes the amount of material covering the vessel lumen. This minimal material is anticipated to allow the tissue to heal faster around and over the stent. The porosity index of the stent and perforated cover may be quite high, comparable to that of conventional stents alone. This can be accomplished by minimizing the amount of material with the structural portion of the stent. Material can be removed because the traditional metal portion of the stent does not need to be optimized for vessel scaffolding, bending uniformity, or other conventionally considered attributes. The coverage of the vessel luminal surface (including the perforated cover and metal stent) is preferably less than 50%, with less than 40%, 30%, or even 20% being possible and usually preferred. These numbers correspond to porosity indices of 50%, 60%, 70%, and 80% respectively.

For the stent provided with the perforated cover, the luminal area covered by the combined stent and cover may be determined using a stent inspection system (e.g., Visicon Finescan, Napa Calif.). Using the inspection system, a 1.0 cm length of the cylindrical device is imaged as a 360 degree flat pattern. The contrast of the image should be sufficient to allow full visualization of the perforated structure and stent. From the flat pattern image, the area of coverage of the stent and perforated cover can then be determined. The percentage of porosity is then determined using the porosity index equation presented above.

The perforated cover provides a favorable substrate to deliver drugs or other therapeutic agents to the vessel. Because the perforated cover has uniformly sized perforations, the elution of the drug into the vessel can be controlled more precisely and uniformly.

The perforated cover structure creates uniform support of the vessel. The opening size in traditional stents or stents covered with a woven material can vary depending on how the stent is bent, on the diameter it achieves within a stenotic vessel, or other factors.

The structure is also highly reliable. For stents constructed with a woven covering, a single broken fiber may unravel and protrude into the vessel lumen. With the perforated cover structures described herein, all web locations are supported by multiple additional webs in close proximity, minimizing the potential for a broken web to protrude into the lumen of the vessel. In addition, the web is fully attached to the stent minimizing the risk of material protruding into the lumen.

Another desirable aspect of the perforated cover is it allows continued access to side branch vessels. A 0.35 mm diameter guide wire can be easily threaded through the wall of the stent with a perforated cover pattern with perforations on the order of about 0.5 mm smallest transverse dimension. This perforation can then be dilated up using an interventional dilator to 1 millimeter diameter. Exchanging a balloon for the dilator, and positioning the balloon through the perforated cover over the guide wire, the perforated cover can be dilated to the desired size. This process opens a transmural hole that would allow passage of other devices (e.g., balloons, stents, etc) into the side branch and minimizes the disruption of the blood flow to the side branch artery.

The stent device shall have sufficient strength to allow, after deploying a partial length of the stent device, the stent device to be repositioned without suffering damage. These forces shall also be greater than the minimum forces required to break the delivery catheter, which may be as defined in ISO 10555-1 as 3N, 5N, 10N, or 15N (depending on the diameter of the catheter). Correspondingly, for the 5 holes per circumference samples with 5 intermediate webs between the holes (Sample B1 and B2 described below), the minimum web tensile strength would be the ISO 10555 values divided by 5 webs, or 0.6N, 1N, 2N, or 3N.

Device tensile strengths were measured in a tensile testing machine. 6 mm and 37 mm diameter stents made as described above were clamped in semi-circular jaw inserts, as shown in FIG. 4P. The jaw inserts were made from stainless steel and had a thickness of approximately 3 mm. The width of the semi-circular cut in the jaw inserts 56 was 5 to 15% larger than half the stent device's circumference; for example, for the 6 mm diameter stent, a 10 mm semi-circular cut jaw insert width was used while for the 37 mm diameter stent, a 65 mm semi-circular jaw insert width was used. This sizing allowed the ends of the device to be flattened and easily fit within the semi-circular feature of the jaw insert 56. This type of jaw insert configuration was selected to maximize the potential for the sample to break away from the clamped jaw insert 56. Data from breaks that occur immediately adjacent to a jaw edge are to be discarded. Gauge length 59 was measured from the top of the semi-circular cut in the top jay insert to the bottom of the semi-circular cut in the bottom jaw insert, as shown in FIG. 4P. To minimize the risk of jaw slippage, the jaw inserts 56 were lined on their inward face with 400 grit sandpaper using double-faced transparent tape. The edge of the semi-circle was also provided with a 1.5 mm radius. These semi-circular jaw inserts 56 were placed within the tensile tester's standard serrated jaws 58, as shown in FIG. 4P. The air pressure to the jaws was set to 0.62 MPa. The tensile tester (Instron model number 5564, Instron Corp., Norwood Mass.) was programmed for a rate of 100% gauge length per minute (rate consistent with ISO 7198 requirements). Using this requirement, the 6 mm diameter stents were tested using a gauge length of 15 mm with a rate of 15 mm/min, while the 37 mm diameter stents were tested using a 40 mm gauge length with a rate of 40 mm/min. All testing occurred at room temperature (24° C.). Device tensile strength was determined at the peak force from initial breakage (away from the jaw inserts) of the perforated cover.

Tensile strength of the web between a pair of adjacent perforations was measured using a fiber was threaded through each of the perforations and around the intervening single web of the perforated cover, as follows. On the bottom jaw of the tensile tester, a rod smaller than the diameter of the stent (i.e., 4.6 mm diameter stainless steel rod) was clamped in the tensile tester's bottom jaw in a horizontal orientation. The stent to be tested was slid onto the rod and against the tensile tester's jaw. A length of fishing line (of about 0.35 mm diameter) was threaded around a single web of the perforated cover by passing the line through two perforations adjacent to the web, in one direction for the first perforation and the opposite direction for the second perforation. Both ends of the fishing line were clamped to the upper jaw of the tensile tester with the air pressure supplied to operate the jaws set at 0.062 MPa. Any smooth fiber or line with a tensile strength of at least 25N and with a diameter smaller than the perforation diameter could be used; smooth-surface fibers are necessary in order to break rather than cut the web between the adjacent perforations. When looping the fiber through a single web of the device, care was taken to assure that only the web, and not any section the metal portion of the stent, was looped. The tensile tester was then run at a jaw separation rate of 100 mm/min (consistent with ISO 7198 requirements for suture retention strength test). Testing was performed at room temperature (24° C.). Web tensile strength was determined from the peak force required to cause the single section of web to break.

Porosity index was also determined for stents provided with the perforated cover. This can be determined using the stent inspection system as described above or by analyzing each component (stent and cover) separately. This is accomplished on a uniformly perforated structure by measuring the area of the nominal perforation and multiplying by the total number of perforations. This is then divided by the total area of the cover, subtracting this value from 100%, resulting in the cover area percentage. The stent area ratio can be determined by using techniques commonly know in the industry (e.g., ASTM F2081).

Bend radius was determined using the method defined in ISO 7198 (1998, section 8.9).

All perforated cover-based device samples were built as described above with the following exceptions. For Samples A1 and A2, the perforated cover was sized to fit on a 6 mm stent where perforated cover aperture sizes were approximately 0.40 to 0.45 mm with about 40 holes per circumference. For Samples B1 and B3, the perforated cover was sized to fit on a 6 mm stent where perforated cover aperture sizes were approximately 4.0-4.2 mm with 5 holes per circumference. For Samples C1 and C3, the perforated cover was sized to fit on a 37 mm stent where perforated cover aperture sizes were approximately 0.40 to 0.45 mm with 220 holes per circumference. For Samples D1 and D3, the perforated cover was sized to fit on a 37 mm stent where perforated cover aperture sizes were 5.5 to 5.6 mm with 20 holes per circumference. For Sample E, the perforated cover was constructed using the same method as for Samples D1 and D2, but the perforated cover was not attached to a stent. All samples had an approximate thickness of 40 microns, as determined by a calibrated snap gauge (Mitutoyo Model ID-C112EB on base Mitutoyo Code 7004).

Samples were tested as described above. Sample A had porosity index of 52% and a web tensile strength of 2.8N. The Sample A2 was bent around a calibrated pin with a diameter of 5.5 mm without kinking. Samples A1 and A2 had a web width of about 60 to 100 microns. Sample B1 had a device tensile strength of 7.0N while Sample B2 had a web tensile strength of 4.4N. Samples B1 and B2 had a porosity index of 78%. The Sample B3 was bent around a calibrated pin with a diameter of 1.5 mm without kinking. Samples B1-B3 had a web width of about 100 to 120 microns. Sample C1 had a device tensile strength of 95.8N while Sample C2 had a web tensile strength of 2.0N. Samples C1 and C2 had a porosity index of 53%. The Sample C3 was bent around a calibrated pin with a diameter of 12.8 mm without kinking. Samples C1-C3 had a web width of about 80 to 90 microns. Sample D1 had a device tensile strength of 20.9N while Sample D2 had a web tensile strength of 4.7N. The Sample D3 was bent around a calibrated pin with a diameter of 6.4 mm without kinking. Samples D1-D3 had a web width of about 120 to 200 microns. Sample E (perforated cover only) had a device tensile strength of 21.0N. Sample D had a porosity index of 82%.

Note that when testing the perforated cover alone (Sample E), the cover's tensile strength for this construct of 20 holes/circumference, corresponding to 20 webs/circumference, was 21N. Other constructs with 10, 5, or 2 holes may be desirable (corresponding to 10, 5, and 2 webs/circumference respectively), with estimated corresponding tensile strengths of 10N, 5N, and 2N respectively.

While particular embodiments of the present invention have been illustrated and described herein, the present invention should not be limited to such illustrations and descriptions. It should be apparent that changes and modifications may be incorporated and embodied as part of the present invention within the scope of the following claims

We claim:

1. An implantable stent defining a length and having a deployed diameter suitable for implantation and a compacted diameter suitable for passage of the stent through a body conduit, the deployed diameter being larger than the compacted diameter of the stent, the implantable stent comprising adjacent metallic stent elements spaced apart longitudinally wherein the adjacent stent elements are connected longitudinally only by a perforated polymeric nonwoven sheet cover, the cover having a multiplicity of individual apertures of substantially uniform size, each of the multiplicity of individual apertures having a long dimension that is parallel to the longitudinal axis of the stent when the stent is at the compacted diameter, each of the multiplicity of individual apertures having a substantially uniform shape when the stent is at the deployed diameter, wherein the multiplicity of individual apertures have a minimum size of about 0.10 mm; and wherein the stent is substantially open, having a porosity index of at least 50% along the length of the stent when the implantable stent is at the deployed diameter.

2. An implantable stent according to claim 1, wherein each of the multiplicity of individual apertures are substantially rectangular when the stent has the compacted diameter.

3. An implantable stent according to claim 1, wherein the minimum aperture size of the multiplicity of individual apertures is about 0.4 mm.

4. An implantable stent according to claim 1, wherein each of the multiplicity of individual apertures are of a substantially hexagonal shape.

5. An implantable stent according to claim 1, wherein each of the multiplicity of individual apertures are of a substantially square shape.

6. An implantable stent according to claim 1 wherein the adjacent stent elements are adjacent helically wound metallic stent elements.

7. An implantable stent according to claim 1, wherein each of the multiplicity of individual apertures are of a substantially triangular shape.

8. An implantable stent according to claim 1, wherein the cover is fully attached to the stent.

9. An implantable stent according to claim 1, wherein the multiplicity of individual apertures include a plurality of longitudinally offset adjacent apertures.

10. An implantable stent according to claim 1, wherein the multiplicity of individual apertures include a plurality of adjacent apertures that are longitudinally offset and overlapping.

11. An implantable stent according to claim 1, wherein each of the multiplicity of individual apertures defines a shape having rounded corners.

12. An implantable stent according to claim 1, wherein the cover has a web tensile strength greater than 0.6N.

13. An implantable stent according to claim 1, wherein the cover has a web tensile strength greater than 2N.

14. An implantable stent according to claim 1, wherein the stent exhibits a device tensile strength greater than 3N.

15. An implantable stent defining a length and having a deployed diameter suitable for implantation and a compacted diameter suitable for passage of the stent through a body conduit, the deployed diameter being larger than the compacted diameter of the stent, the implantable stent comprising adjacent metallic stent elements spaced apart longitudinally wherein the adjacent stent elements are connected longitudinally only by a perforated polymeric non-woven sheet cover that limits axial expansion between the adjacent metallic stent elements, the cover having a multiplicity of individual apertures of substantially uniform size, each of the multiplicity of individual apertures having a long dimension that is parallel to the longitudinal axis of the stent when the stent is at the compacted diameter, each of the multiplicity of individual apertures having a substantially uniform shape when the stent is at the deployed diameter, wherein the multiplicity of individual apertures have a minimum size of about 0.10 mm; and wherein the stent is substantially open, having a porosity index of at least 50% along the length of the stent when the implantable stent is at the deployed diameter.

* * * * *